(12) United States Patent  (10) Patent No.: US 8,491,306 B2
Raby et al.  (45) Date of Patent: Jul. 23, 2013

(54) REGISTERING PHYSICAL AND VIRTUAL TOOTH STRUCTURES WITH PEDESTALS

(75) Inventors: Richard E. Raby, North St. Paul, MN (US); James D. Cleary, Glendora, CA (US); Oliver L. Puttler, La Crescenta, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 1607 days.

(21) Appl. No.: 11/195,954

(22) Filed: Aug. 3, 2005

(65) Prior Publication Data

US 2007/0031790 A1 Feb. 8, 2007

(51) Int. Cl.
*A61C 11/00* (2006.01)

(52) U.S. Cl.
USPC .......................................... 433/213; 433/214

(58) Field of Classification Search
USPC .......... 433/213–218, 223–224, 24, 6; 409/96, 409/84, 219, 221, 225; 345/419, 420; 382/209, 382/217, 218, 128; 700/97–98, 118
See application file for complete search history.

(56) References Cited

U.S. PATENT DOCUMENTS

| | | | |
|---|---|---|---|
| 5,027,281 A | 6/1991 | Rekow et al. | |
| 5,256,064 A | 10/1993 | Riihimaki et al. | |
| 5,762,492 A | 6/1998 | Kanomi et al. | |
| 5,848,115 A * | 12/1998 | Little et al. | 378/4 |
| 6,099,314 A | 8/2000 | Kopelman et al. | |
| 6,123,544 A * | 9/2000 | Cleary | 433/24 |
| 6,200,135 B1 | 3/2001 | Hultgren | |
| 6,206,693 B1 | 3/2001 | Hultgren | |
| 6,217,334 B1 | 4/2001 | Hultgren | |
| 6,227,850 B1 | 5/2001 | Chishti et al. | |
| 6,322,359 B1 | 11/2001 | Jordan et al. | |
| 6,579,095 B2 * | 6/2003 | Marshall et al. | 433/213 |
| 6,621,491 B1 | 9/2003 | Baumrind et al. | |
| 6,648,640 B2 * | 11/2003 | Rubbert et al. | 433/24 |
| 6,767,208 B2 | 7/2004 | Kaza | |
| 6,882,894 B2 | 4/2005 | Durbin et al. | |
| 6,979,196 B2 | 12/2005 | Nikolskiy et al. | |
| 7,172,417 B2 | 2/2007 | Sporbert et al. | |
| 2002/0081554 A1 * | 6/2002 | Marshall et al. | 433/213 |
| 2002/0110786 A1 * | 8/2002 | Dillier | 433/213 |
| 2002/0197581 A1 | 12/2002 | Georgakis et al. | |
| 2003/0009252 A1 | 1/2003 | Pavlovskaia et al. | |
| 2003/0052785 A1 * | 3/2003 | Gisselberg et al. | 340/572.8 |
| 2003/0068079 A1 | 4/2003 | Park | |
| 2003/0129565 A1 | 7/2003 | Kaza | |
| 2003/0203334 A1 * | 10/2003 | Hedge et al. | 433/53 |
| 2003/0207227 A1 * | 11/2003 | Abolfathi | 433/24 |
| 2003/0224316 A1 * | 12/2003 | Marshall | 433/24 |
| 2004/0133293 A1 * | 7/2004 | Durbin et al. | 700/98 |
| 2004/0172150 A1 * | 9/2004 | Perot et al. | 700/98 |

(Continued)

OTHER PUBLICATIONS

Pending U.S. Appl. No. 11/275,167, filed Dec. 16, 2005.

(Continued)

*Primary Examiner* — Yogesh Patel

(57) ABSTRACT

In general, the invention relates to techniques for registering a three-dimensional (3D) coordinate system of a physical model of a patient's tooth structure to a 3D coordinate system of a virtual model of the same tooth structure. Techniques are described to register the complex geometries of the physical and virtual tooth structures by using a known physical characteristic of a pedestal associated with the physical model.

38 Claims, 17 Drawing Sheets

U.S. PATENT DOCUMENTS

| | | |
|---|---|---|
| 2004/0185422 A1 | 9/2004 | Orth et al. |
| 2004/0191719 A1 | 9/2004 | Kaza |
| 2005/0043837 A1* | 2/2005 | Rubbert et al. ............ 700/98 |
| 2005/0106528 A1 | 5/2005 | Abolfathi et al. |
| 2005/0106529 A1 | 5/2005 | Abolfathi et al. |
| 2005/0130095 A1 | 6/2005 | Raby et al. |
| 2005/0153257 A1* | 7/2005 | Durbin et al. ............ 433/68 |
| 2005/0170309 A1 | 8/2005 | Raby et al. |
| 2005/0244790 A1 | 11/2005 | Kuperman |
| 2005/0250075 A1* | 11/2005 | Taub et al. ............ 433/213 |
| 2006/0275731 A1 | 12/2006 | Wen et al. |
| 2006/0275736 A1* | 12/2006 | Wen et al. ............ 433/213 |

OTHER PUBLICATIONS

Pending U.S. Appl. No. 11/195,952, filed Aug. 3, 2005.
Pending U.S. Appl. No. 11/195,955, filed Aug. 3, 2005.
Casko et al., "Objective grading system for dental casts and panoramic radiographs", American Journal of Orthodontics and Dentofacial Orthopedics, vol. 114, No. 5, pp. 589-599 (Nov. 1998).
Moskowitz et al., A New Look at Indirect Bonding, Journal of Clinical Orthodontics, 1996, vol. XXX, No. 5, pp. 277-281.

* cited by examiner

REGISTERING PHYSICAL AND VIRTUAL TOOTH STRUCTURES WITH PEDESTALS

TECHNICAL FIELD

The invention relates to orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

In general, orthodontic appliances that are adapted to be adhesively bonded to the patient's teeth are placed on the teeth by either one of two methods: a direct bonding method, or an indirect bonding method. In the direct bonding method, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place. Typical adhesives include light-curable adhesives that begin to harden upon exposure to actinic radiation, and two-component chemical-cure adhesives that begin to harden when the components are mixed together.

While the direct bonding technique described above is in widespread use and is considered satisfactory by many, there are shortcomings that are inherent with such a technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally bumped from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some time may be necessary before the practitioner is satisfied with the location of each appliance. At the same time, however, the patient may experience discomfort and have difficulty in remaining relatively motionless, especially if the patient is an adolescent. As can be appreciated, there are aspects of the direct bonding technique that can be considered a nuisance for both the practitioner and for the patient.

Indirect bonding techniques often avoid many of the problems noted above. In general, indirect bonding techniques known in the past have involved the use of a transfer tray having a shape that matches the configuration of at least part of a patient's dental arch. A set of appliances such as brackets are releasably connected to the tray at certain, predetermined locations. Adhesive is applied to the base of each appliance, and the tray is then placed over the patient's teeth until such time as the adhesive hardens. Next, the tray is detached from the teeth as well as from the appliances, with the result that all of the appliances previously connected to the tray are now bonded to the respective teeth at their intended, predetermined locations.

In more detail, one method of indirect bonding of orthodontic appliances includes the steps of taking an impression of each of the patient's dental arches and then making a replica plaster or "stone" model from each impression. Optionally, a soap solution (such as Model Glow brand solution from Whip Mix Corporation) or wax is applied to the stone model. A separation solution (such as COE-SEP brand tinfoil substitute from GC America, Inc.) is then applied to the stone model and allowed to dry. If desired, the teeth of the model can be marked with a pencil to assist in placing the brackets in ideal positions.

Next, the brackets are bonded to the stone models. Optionally, the bonding adhesive can be a chemical curing adhesive (such as Concise brand adhesive from 3M) or a light-curable adhesive (such as Transbond XT brand adhesive or Transbond LR brand adhesive, from 3M). Optionally, the brackets may be adhesive precoated brackets such as those described in U.S. Pat. Nos. 5,015,180, 5,172,809, 5,354,199 and 5,429,299.

A transfer tray is then made by placing a matrix material over the model as well as over the brackets placed on the model. For example, a plastic sheet matrix material may be held by a frame and exposed to radiant heat. Once the plastic sheet material has softened, it is placed over the model and the brackets. Air in the space between the sheet material and the model is then evacuated, and the plastic sheet material assumes a configuration that precisely matches the shape of the replica teeth of the stone model and the attached brackets.

The plastic material is then allowed to cool and harden to form a tray. The tray and the brackets (which are embedded in an interior wall of the tray) are then detached from the stone model and sides of the tray are trimmed as may be desired. Once the patient has returned to the office, a quantity of adhesive is placed on the base of the bracket, and the tray with the embedded brackets is then placed over the matching portions of the patient's dental arch. Since the configuration of the interior of the tray closely matches the respective portions of the patient's dental arch, each bracket is ultimately positioned on the patient's teeth at precisely the same location that corresponds to the previous location of the same bracket on the stone model.

Both light-curable adhesives and chemical curing adhesives have been used in the past in indirect bonding techniques to secure the brackets to the patient's teeth. If a light-curable adhesive is used, the tray is preferably transparent or translucent. If a two-component chemical curing adhesive is used, the components can be mixed together immediately before application of the adhesive to the brackets. Alternatively, one component may be placed on each bracket base and the other component may be placed on the tooth surface. In either case, placing of the tray with the embedded brackets on corresponding portions of the patient's dental arch enables the brackets to be bonded to the teeth as a group using only a short amount of time that the patient is occupying the chair in the operatory. With such a technique, individual placement and positioning of each bracket in seriatim fashion on the teeth is avoided.

A variety of transfer trays and materials for transfer trays have been proposed in the past. For example, some practitioners use a soft sheet material (such as Bioplast tray material from Scheu-Dental GmbH or Great Lakes Orthodontics, Ltd.) for placement over the stone model and the appliances on the model. Either a vacuum or positive pressure is applied to respectively pull or push the soft material into intimate contact with the model and the appliances on the model. Next, a stiffer sheet material (such as Biocryl sheet material, from Scheu-Dental GmbH or Great Lakes Orthodontics, Ltd.) is formed over the softer sheet material, again using a either a vacuum or positive pressure forming technique. The stiffer material provides a backbone to the tray, while the softer material initially holds the appliances and yet is sufficiently flexible to release from the appliances after the appliances have been fixed to the patient's teeth.

It has also been proposed in the past to use a silicone impression material or a bite registration material (such as Memosil 2, from Heraeus-Kulzer GmbH-& Co. KG). The silicone material is applied over the appliances that are attached to the study model so that the appliances are partially encapsulated.

In an article entitled "A New Look at Indirect Bonding" by Moskowitz et al. (Journal of Clinical Orthodontics, Volume XXX, Number 5, May 1996, pages 277 et sec.), a technique for making indirect bonding trays is described using Reprosil impression material (from Dentsply International). The impression material is placed with a syringe over brackets that have been previously placed on a stone model. Next, a sheet of clear thermoplastic material is drawn down over the impression material using a vacuum-forming technique. The resultant transfer tray is then removed from the model for subsequent placement on the patient's dental arch.

Indirect bonding techniques offer a number of advantages over direct bonding techniques. For one thing, and as indicated above, it is possible to bond a plurality of brackets to a patient's dental arch simultaneously, thereby avoiding the need to bond each appliance in individual fashion. In addition, the indirect bonding tray helps to locate all of the brackets in their proper, intended positions such that adjustment of each bracket on the surface of the tooth before bonding is avoided. The increased placement accuracy of the appliances that is often afforded by indirect bonding techniques helps ensure that the patient's teeth are moved to their proper, intended positions at the conclusion of treatment.

The state of the art in orthodontics is rapidly moving toward digital and computer-aided techniques. These techniques include the use of intra and extra-oral scanners, three-dimensional (3D) modeling of a tooth structure, and fabrication of orthodontic devices from digital data.

SUMMARY

In general, the invention relates to techniques for registering a three-dimensional (3D) coordinate system of a physical model of a patient's tooth structure to a 3D coordinate system of a virtual model of the same tooth structure. Techniques are described to register the complex geometries of the physical and virtual tooth structures by using a known physical characteristic of a pedestal associated with the physical model.

As one example, a pedestal having a known geometry may be physically attached to a casting model prior to scanning the casting model in order to generate a digital model of the casting and the pedestal. The known geometry of the pedestal may then be used to assist registration of the coordinate system of the physical casting to the coordinate system of the 3D digital model for creation of a digital orthodontic prescription for the patient. Furthermore, the known geometry of the pedestal may mate with a fixture of manufacturing equipment for automated appliance manufacturing (e.g., indirect bonding tray fabrication) based on the digital prescription.

Other example techniques described herein utilize a pedestal with fiducial markers embedded at known locations, a pedestal mated to an impression tray with dimples at known locations, or a virtual pedestal of known physical characteristic attached to a digital model of a tooth structure within a virtual computer environment.

In one embodiment, a method comprises forming a physical model of a patient's tooth structure, attaching a pedestal having a known physical characteristic to the physical model, scanning the physical model with the pedestal to generate a digital model of the tooth structure, and registering the physical model to the digital model based on the known physical characteristic of the pedestal. The method further comprises forming an indirect bonding device with the registered physical and digital models.

In another embodiment, an apparatus comprises a physical model of a patient's tooth structure, and a pedestal having a known physical characteristic adapted for registration of the pedestal and physical model within a 3D environment, wherein the pedestal is attached to the physical model.

In another embodiment, an apparatus comprises a main pedestal having posts, an impression tray having dimples that mate to the posts of the main pedestal; a casting material inside of the impression tray, and an inverted pedestal having screws which come into contact with the casting material.

In another embodiment, a system comprises a physical model of a tooth structure attached to a pedestal having a known physical characteristic, a scanner that scans the physical model with attached pedestal to generate a digital model of the tooth structure, a computer that registers the physical model to the digital model with the known physical characteristic of the pedestal. The system further comprises forming an indirect bonding device with the registered physical and digital models.

In another embodiment, a method comprises generating a digital model of a tooth structure, attaching a virtual pedestal of known physical characteristic to the digital model, and generating a physical model of the tooth structure with attached pedestal of known physical characteristic from the digital model with the attached virtual pedestal of known physical characteristic.

The invention may provide one or more advantages. For example, the techniques may provide for assisted (e.g., automatic or semi-automatic) registration of physical and virtual models used during indirect bonding tray fabrication. Assisted registration may reduce the labor, cost, and probability of error during manufacturing of an orthodontic appliance, such as an indirect bonding tray. The details of one or more embodiments of the invention are set forth in the accompanying drawings and the description below. Other features, objects, and advantages of the invention will be apparent from the description and drawings, and from the claims.

DETAILED DESCRIPTION

Figure 1:
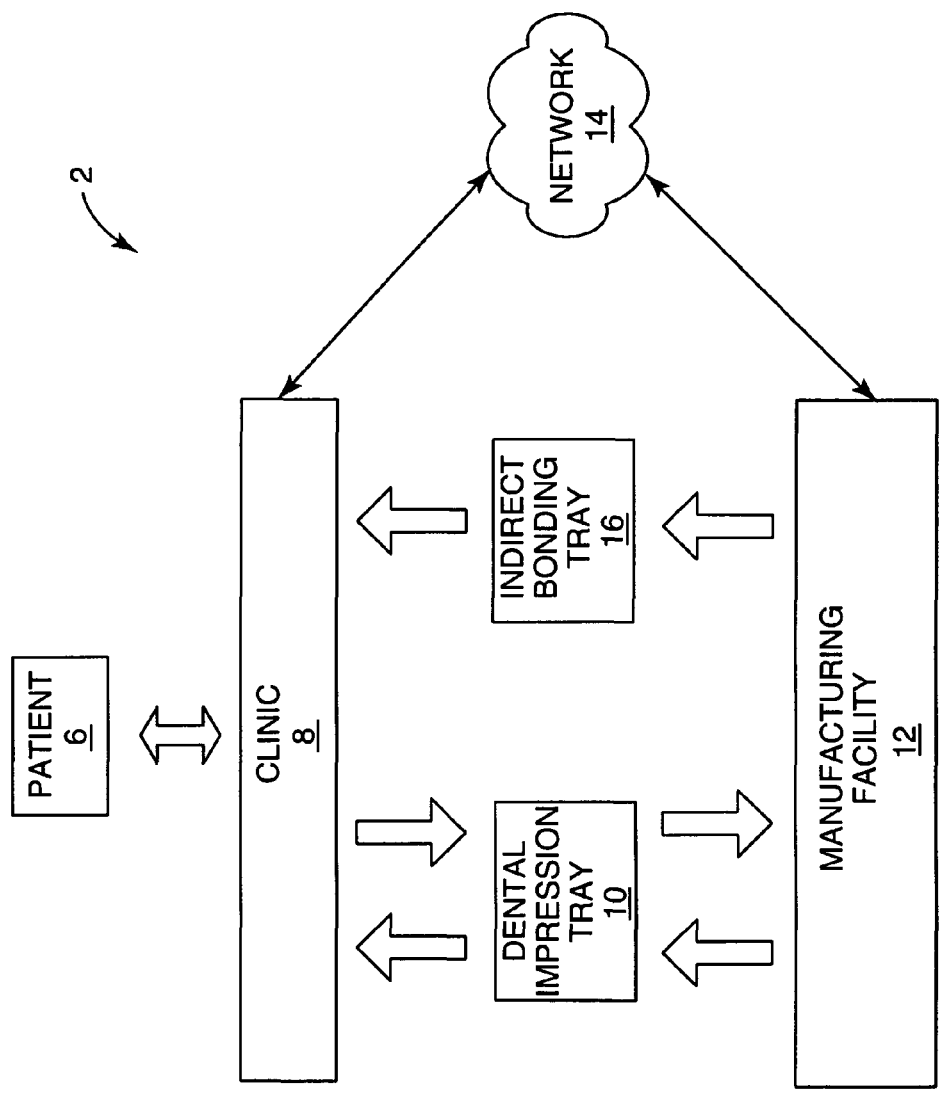
FIG. 1 is a block diagram illustrating an exemplary computer environment 2 in which a clinic and a manufacturing facility communicate information throughout an indirect bonding tray manufacturing process.

FIG. 1 is a block diagram illustrating an exemplary computer environment 2 in which a clinic and a manufacturing facility communicate information throughout an indirect bonding tray manufacturing process. Although described with respect to manufacturing of indirect bonding trays, the techniques may be applied to other computer-implemented processes for assisting orthodontic diagnosis and treatment.

Initially, manufacturing facility 12 produces a dental impression tray 10 for receiving dental impressions of a dental arch or other tooth structure of patient 6. Manufacturing facility 12 ships dental impression tray 10 to clinic 8. The dental impression tray 10 is loaded with a quantity of impression material just prior to taking the impression at clinic 8, or alternatively is preloaded with quantity of impression material by the manufacturer before shipment to the clinic. Impression tray 10 is adapted to extend along the entire dental arch, although as an alternative it is possible to use an impression tray that extends along a fewer number of teeth such as a dental quadrant.

An orthodontic practitioner of clinic 8 utilizes dental impression tray 10 to capture an impression of the dental arch of patient 6. Clinic 8 stores digital information in a patient record within a database to associate the patient record with the particular dental impression tray 10. Clinic 8 may, for example, update a local database having a plurality of patient records. Alternatively, clinic 8 may remotely update a central database within manufacturing facility 12 via network 14.

In either case, clinic 8 then returns dental impression tray 10 to manufacturing facility 12. Manufacturing facility 12 utilizes dental impression tray 10 to construct an indirect bonding tray 16 for use in physically placing brackets on the teeth of patient 6.

Construction of indirect bonding tray 16 involves a multi-step process conducted at manufacturing facility 12. First, manufacturing facility 12 creates a casting from dental impression tray 10. The term "casting" is used generally herein to refer to any type of physical model made from dental impression tray 10, for example, a replica made from plaster of Paris or from a polymeric material such as an epoxy that transmits actinic radiation. Suitable epoxy and other polymeric materials are described in published U.S. patent application 20040219473, which is incorporated by reference herein. The term "casting" is also used generally herein to refer to a physical model of predicted tooth positions, such as a stereolithographic model used in the fabrication of tooth positioning trays. Examples of tooth positioning trays include those sold by Align Technology of Santa Clara, Calif. and those described in U.S. Pat. Nos. 6,309,215 and 6,705,863, both of which are incorporated by reference herein. Optionally, in instances where a digital model of the entire arch is not needed, the casting may include a fewer number of teeth than the number of teeth represented in the impression.

In certain embodiments, the casting contains or is affixed to one or more registration components having known physical characteristics. The registration components may have been placed into the impression tray at clinic 8 and transferred to the casting or may have been attached to or embedded within the casting at manufacturing facility 12.

Next, manufacturing facility 12 scans the casting or the impression with one or more registration components to generate a three-dimensional (3D) digital model of the tooth structure. Multiple castings or impressions may be scanned simultaneously to reduce the number of scans. For example, scanning a casting of a patient's upper jaw along with a casting of the patient's lower jaw and bite impression enables registration of the models relative to each other (for setting the bite) along with registration of the castings to the virtual models all in a single scan. The registration components enable manufacturing facility 12 to utilize the digital model for receiving prescription data and bracket placement data from clinic 8 in order to automatically place brackets onto the casting per the clinic's specifications. Manufacturing facility 12 then forms indirect bonding tray 16 from the casting with the affixed brackets. Lastly, manufacturing facility 12 forwards indirect bonding tray 16 to clinic 8 for use in a conventional indirect bonding procedure to place the brackets on the teeth of patient 6.

Manufacturing facility 12 may produce indirect bonding tray 16 by placing a matrix material in the form of a plastic sheet over the casting and the brackets and exposing the matrix material to radiant heat. Air in the space between the sheet material and the casting is then forced out by a pressure differential between the inner and outer surfaces of the sheet material (i.e. either by vacuum forming or positive pressure forming), and the plastic sheet material assumes a configuration that precisely matches the shape of the replica teeth of the casting and the attached brackets. Suitable indirect bonding trays and methods for making indirect bonding trays are described, for example, in copending and commonly assigned U.S. patent application Ser. No. 10/428,301 entitled "Method and Apparatus for Indirect Bonding of Orthodontic Appliances", filed May 2, 2003 to Cleary et al., Ser. No. 10/428,255 entitled "Orthodontic Appliances Having a Contoured Bonding Surface", filed May 2, 2003 to Cleary et al., and Ser. No. 10/678,841 entitled "Method and Apparatus for Bonding Orthodontic Appliances to Teeth", filed Oct. 3, 2003 to Cleary et al., all of which are entirely incorporated herein by reference.

As further described, techniques may be used to assist (e.g., automatically or semi-automatically) registration of a physical model to a corresponding digital model for automated appliance manufacturing, such as manufacturing of an indirect bonding device from the casting. For example, the techniques involve attaching or embedding one or more registration components of known physical characteristic to a physical model of a patient's tooth structure (e.g., a dental impression, bite registration, or casting) prior to scanning the physical model. For example, the registration component may be a pedestal of known geometry, a pedestal with embedded fiducial markers at known locations, a pedestal attached to an impression tray containing dimples at known locations, a group of three or more tooth markers placed directly on a select number of a patient's teeth prior to forming the impression, or a group of three or more tooth markers placed on an impression or casting after forming the impression or casting. The phrase "patient's tooth structure" is used generally herein to refer to a replica of the patient's current tooth structure and alternatively to a replica of the patient's predicted tooth structure such as may be expected to occur after orthodontic treatment has commenced.

After scanning the physical model with attached registration component or components, a computer registers the coordinate system of the physical model to the coordinate system of the digital model using the known geometry of the pedestal or the known location of the fiducial markers within the pedestal or within the impression tray. Furthermore, the computer may use the known geometry or known location of the registration components to register the coordinate systems of the physical and digital models to the coordinate system of a manufacturing device for automatic bracket placement onto the casting. Lastly, an indirect bonding device is formed upon the casting with the attached brackets.

The invention may provide one or more advantages. The techniques may provide for assisted registration of physical and virtual models used during manufacturing of an orthodontic appliance, such as an indirect bonding tray, an individual or set of machined orthodontic brackets, a buccal tube, a sheath, a button, an arch wire or other orthodontic appliances. The techniques may also enable simultaneous scanning of multiple components utilized during the virtual modeling and automatic bracket placement process. Automatic registration and simultaneous scanning may reduce the labor, cost, and probability of error during multiple steps of orthodontic appliance manufacturing, such as: scanning, registering, virtual bracket placement, physical bracket placement, trimming of an indirect bonding tray or machining an appliance. The invention may also enable the use of roughly formed castings, thereby eliminating the expense of machining plaster casts.

Figure 2:
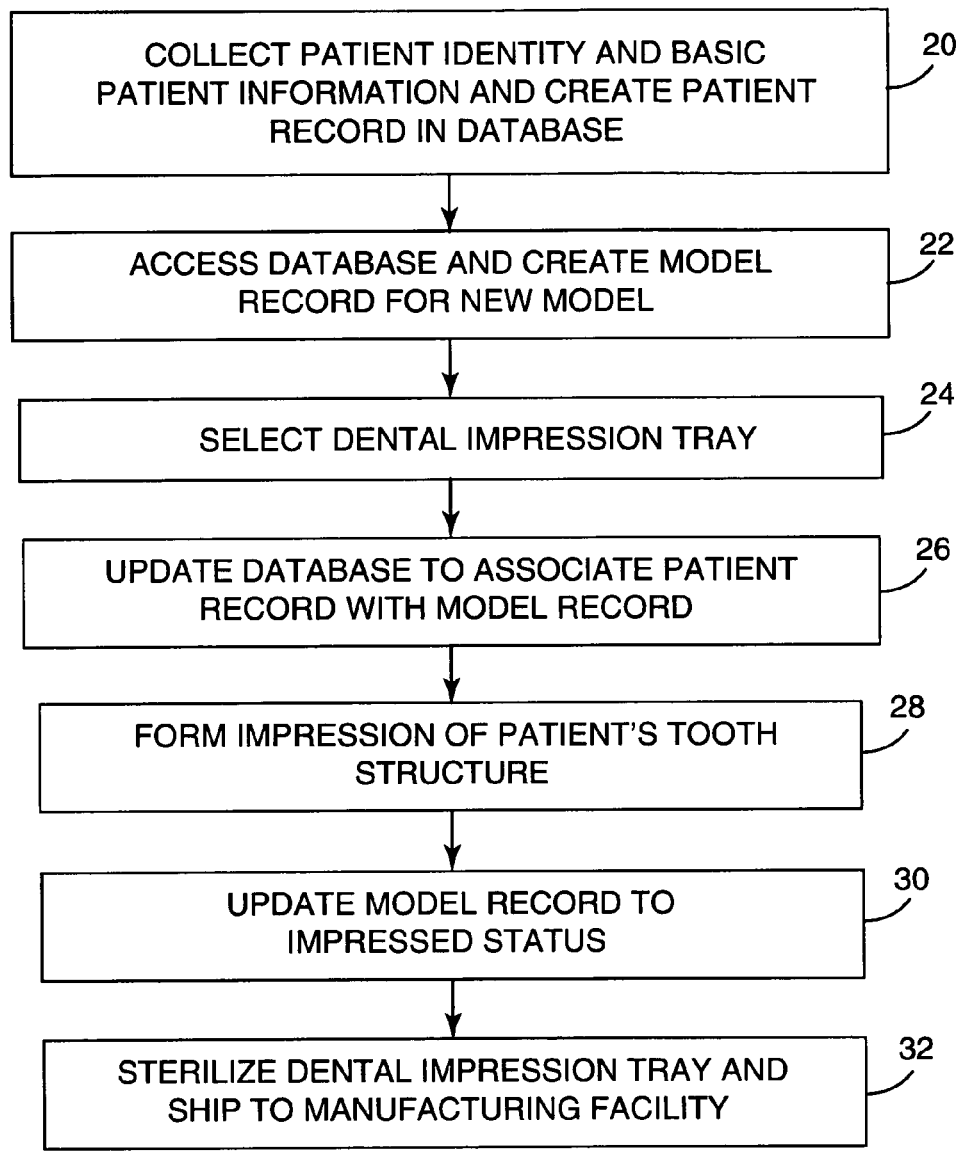
FIG. 2 is a block diagram illustrating an exemplary process at a clinic.

FIG. 2 is a block diagram illustrating a process conducted at clinic 8 in accordance with one embodiment of the invention. Initially, practitioner at clinic 8 collects patient identity and other information from patient 6 and creates a patient record (20). As described, the patient record may be located within clinic 8 and optionally configured to share data with a database within manufacturing facility 12. Alternatively, the patient record may be located within a database at manufacturing facility 12 that is remotely accessible to clinic 8 via network 14.

When capturing an impression of the tooth structure of patient 6, or shortly before or after, practitioner at clinic 8 creates a model record for the new model (22). In the field of orthodontics, the term model refers to any replication of the patient's tooth structure, for example the impression, bite registration, the casting, and/or the 3D digital model of the tooth structure. Practitioner at clinic 8 selects a dental impression tray (24) and then updates the database to associate the appropriate patient record with the model record (26). This model record resides in the database and tracks the status and all variations of data of the patient's tooth structure. The practitioner of clinic 8 then utilizes dental impression tray 10 to form an impression of the patient's tooth structure (28) and updates the model record to the "impressed" status (30). Often times a patient requires orthodontic treatment on both the upper and lower arches. In this case, practitioner at clinic 8 selects impression tray 10 for each arch (24), forms an impression of each arch (28), associates a model record with each arch (26), and updates model record to "impressed" status for each arch (30). Clinic 8 sterilizes or disinfects impression tray 10 and ships the tray to manufacturing facility 12 (32).

Figure 3A:
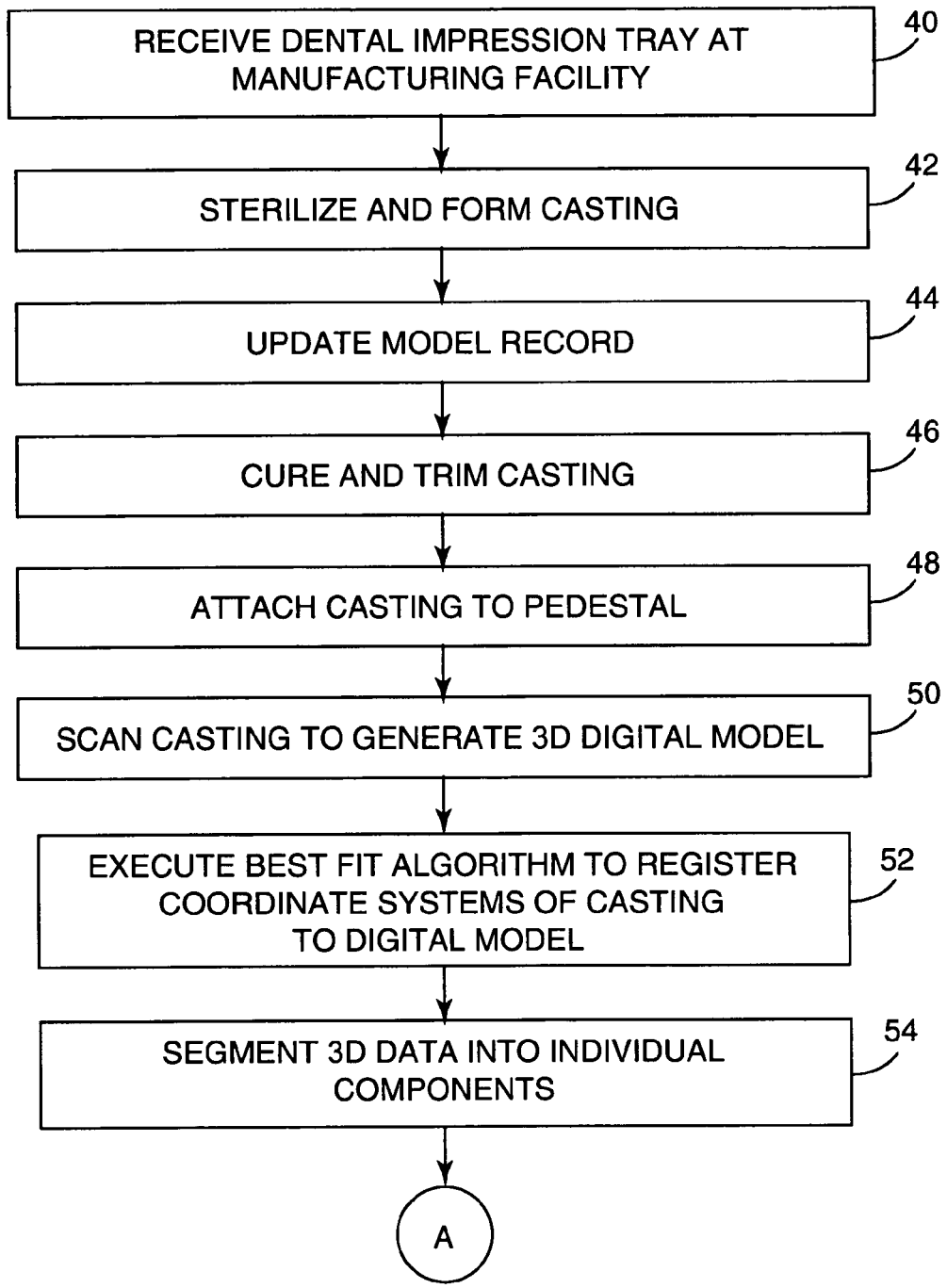
FIGS. 3A and 3B are block diagrams illustrating an exemplary process at an indirect bonding device manufacturing facility.
Figure 3B:
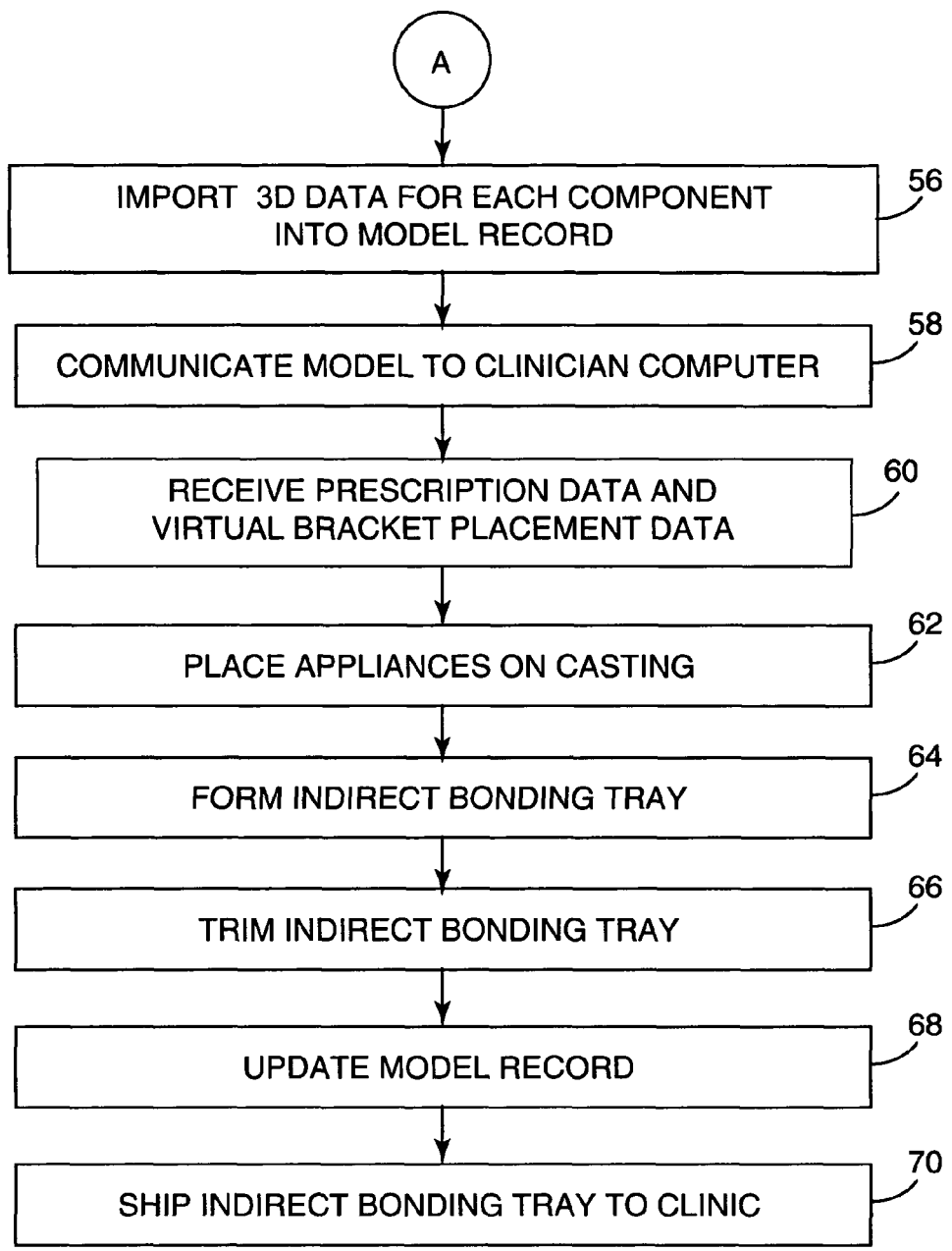

FIGS. 3A and 3B are block diagrams illustrating a process performed by manufacturing facility 12 in accordance with one embodiment of the invention. Manufacturing facility 12 typically receives dental impression tray 10 as part of a larger shipment containing multiple dental impressions (40). Next, manufacturing facility 12 sterilizes or disinfects the shipment of impression trays, including dental impression tray 10, and moves the dental impression trays to a casting station where castings are made from the trays (42). Manufacturing facility 12 then utilizes the same database accessed by clinic 8 to update the model record to indicate a "casting formed" status (44). Next, manufacturing facility 12 cures and trims the casting (46).

In this example, manufacturing facility 12 then attaches a pedestal having known physical characteristics to the casting (48). In one embodiment, the pedestal has a known geometry. Alternatively, or in addition, the pedestal may have embedded fiducial markers, dimples or other physical characteristics. The pedestal may be constructed from plastic, but may alternatively be constructed of other materials. Next, manufacturing facility 12 may utilize a Computed Tomographic (CT) scanner to scan the casting (50). The casting may also be scanned with X-rays, magnetic resonance images or other scanning devices. In cases where a patient requires orthodontic treatment on both the upper and lower arches, castings of the upper and lower arches may be scanned simultaneously (50). The scan generates a point cloud data file which manufacturing facility 12 then surfaces using one of several software packages available on the market today. For example manufacturing facility 12 may utilize a software package called "Wrap" or "Studio" available from Raindrop Geomagic, Inc. of Durham, N.C. Once the point cloud is surfaced, a 3D digital model of the casting with pedestal exists in the computer.

Manufacturing facility 12 then executes a best fit algorithm for automatic or semi-automatic registration between a 3D coordinate system of the physical casting and a 3D coordinate system associated with the digital model of the casting within a 3D modeling environment (52). A computer may automate the registration process by temporarily masking out the casting data to determine a best fit between the scanned pedestal data in a point cloud format and a pre-existing Computer Aided Design (CAD) file of the pedestal of known geometry. For example, the computer may test numerous orientations of the scanned data of the physical pedestal relative to the pedestal CAD data. The registration is complete when the computer determines the best-fit orientation within a predetermined tolerance. This process may be fully automated or semi-automated in that user verification or other input may be requested. The computer then unmasks the casting data within the 3D modeling environment. The best-fit algorithm may be further simplified by attaching the pedestal of the known geometry to a fixture in the scanner prior to scanning the pedestal and the casting. In this manner, the scan may be automatically produced in a relatively known orientation, and the best fit algorithm may be initialized based on this known orientation.

Once the coordinate systems of the physical casting and digital model of the casting are registered within the 3D environment (52), manufacturing facility 12 utilizes software to segment the digital model into individual components prior to virtual bracket placement on the digital model (54). The separation software identifies each tooth and separates the teeth from each other and from the gingiva within the 3D environment. This may be useful in allowing each tooth to independently move within the 3D environment and illustrate the predicted results of any orthodontic prescription.

Manufacturing facility 12 then imports the 3D data for each component from the digital model into the database's model record (56) and communicates model record to clinic 8 (58). After clinic 8 utilizes the model record for virtual bracket placement, manufacturing facility 12 receives prescription data and virtual placement data from clinic 8 (60). The prescription data specifies the individual appliances (e.g. brackets or arch wires) associated with the prescription, and the virtual placement data specifies the location of the appliances within the 3D modeling environment.

Next the physical casting and affixed pedestal travels to a manufacturing station within manufacturing facility 12, where appliances are automatically selected and applied to the casting based on the prescription data and virtual placement data (62). The registration determined between the physical casting and the virtual model of the casting may be used to ensure accurate positioning of the appliances. Further, the pedestal attached to the casting may securely mate with a predefined fixture within the manufacturing equipment to further ensure accurate appliance placement on the physical casting. Example robotic placement devices are described in commonly assigned U.S. Pat. No. 6,123,544, entitled "Method and apparatus for precise bond placement of orthodontic appliances", issued Sep. 26, 2000 to James D. Cleary, and U.S. patent application Ser. No. 11/015368, entitled "RFID tracking of patient-specific orthodontic materials," filed Dec. 17, 2004, both of which are hereby incorporated by reference.

After the manufacturing equipment attaches brackets to the casting, the manufacturing facility 12 forms an indirect bonding tray (64). For example, manufacturing facility 12 may place a heated plastic sheet matrix material over the casting and the brackets so that plastic sheet material assumes a configuration that precisely matches the casting.

Next, manufacturing facility 12 trims the indirect bonding tray (66). Manufacturing facility 12 may utilize automated tray trimming equipment, such as laser or Computer Numerical Control (CNC) cutting devices, to trim the indirect bonding tray. The known geometry of the pedestals registers the coordinate system of the casting with the coordinate system of the tray trimming equipment for trimming the indirect bonding tray while it remains attached to the casting. Since the indirect bonding tray is formed on a casting that is attached to a pedestal of known geometry, the coordinate system associated with the digital representation of the casting may be transferred to a model of the indirect bonding tray, which may in turn be used to automatically control the tray trimming equipment for trimming the indirect bonding tray. At the completion of the indirect bonding tray trimming, manufacturing facility 12 updates the model record to the "trimmed" status (68). Finally, manufacturing facility 12 ships indirect bonding tray 16 to clinic 8 (70).

Figure 4:
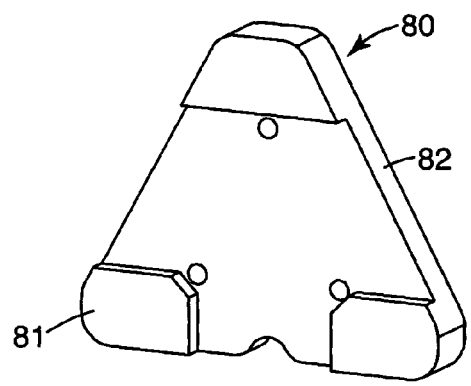
FIG. 4 is a perspective view of an exemplary pedestal of known geometry.

FIG. 4 is a perspective view of an exemplary pedestal 80 of known geometry. Pedestal 80 may be of any shape of known geometry that is able to be manufactured within a specified tolerance. Accordingly, the invention is not limited to the shape and physical characteristics of pedestal 80 illustrated in FIG. 4. Manufacturing facility 12 attaches the casting to a first surface 81 illustrated in FIG. 4. The attachment may be performed in many ways, such as bonding with an adhesive or epoxy, welding by melting and re-solidifying portions of one or both surfaces, screwing, snap-fitting protrusions on the pedestal into holes in the casting, latching, clamping, and the like. A reverse surface 82 of pedestal 80 may be formed so as to mate with a fixture of manufacturing equipment, such as a robotic device, for automatic bracket placement.

Figure 5A:
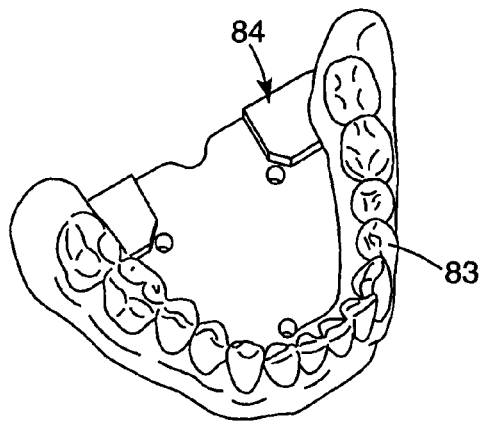
FIGS. 5A and 5B are perspective views of a digital model of a casting attached to a pedestal.
Figure 5B:
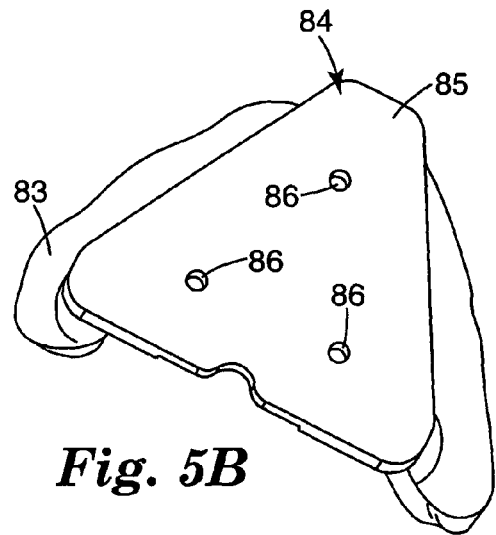

FIGS. 5A and 5B illustrate perspective views of the digital model of a casting 83 attached to a pedestal 84 within a 3D environment. For purposes of illustration, digital pedestal 84 is the digital version of the physical pedestal 80 illustrated in FIG. 4. FIG. 5A illustrates a perspective top view of casting 83 attached to pedestal 84. FIG. 5B illustrates a perspective bottom view of pedestal 84 with the attached casting 83. The bottom surface 85 of pedestal 84 includes three recesses 86 that mate with manufacturing equipment for automatic bracket placement.

Figure 6:
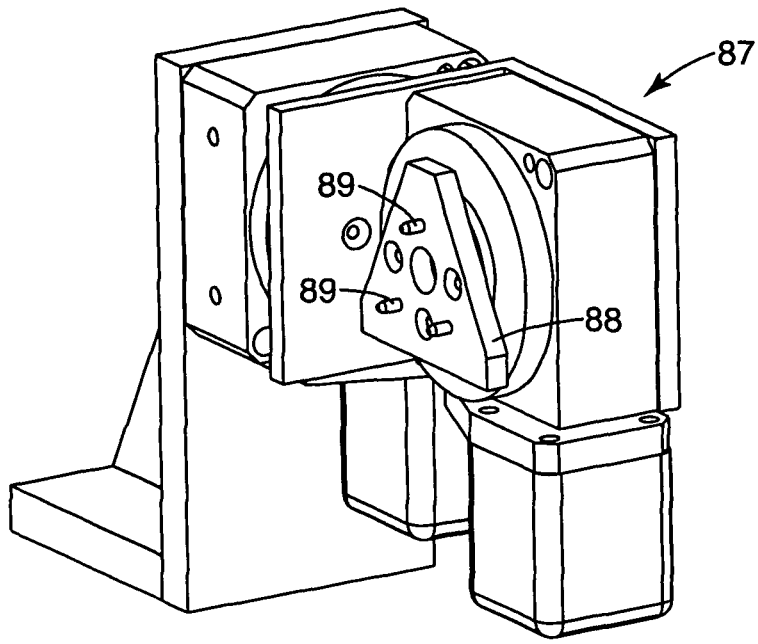
FIG. 6 is a perspective view of an exemplary fixture of a robotic device.

FIG. 6 illustrates a perspective view of an exemplary fixture of a robotic device 87. In this example, fixture 88 includes three pegs 89 that mate with recesses 86 of pedestal 80. (FIGS. 4, 5A and 5B). Fixture 88 may be of any shape that securely fixes a pedestal within a relatively known orientation; thus, the invention is not limited to the fixture illustrated in FIG. 6.

Figure 7:
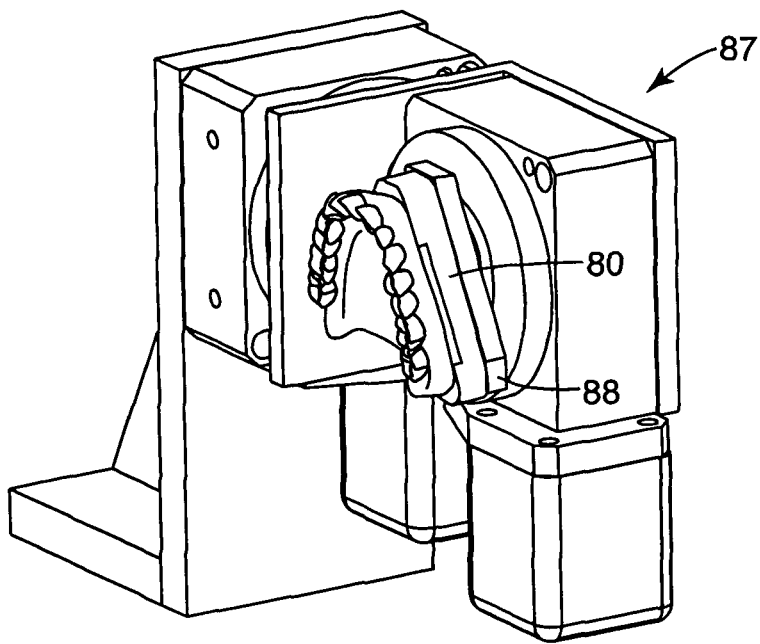
FIG. 7 is a perspective view of an exemplary pedestal with attached model mated to an exemplary fixture of a robotic device.

FIG. 7 illustrates a perspective view of an exemplary pedestal 80 mating to the exemplary fixture 88 of the robotic device 87. The mating of the physical pedestal to the robotic device fixture aligns the physical pedestal in a known orientation relative to robotic device 87. Robotic device may then utilize the registered coordinate systems of the digital models of the pedestal and the casting to place brackets on the physical casting based on the prescription data provided by the clinic.

Figure 8:
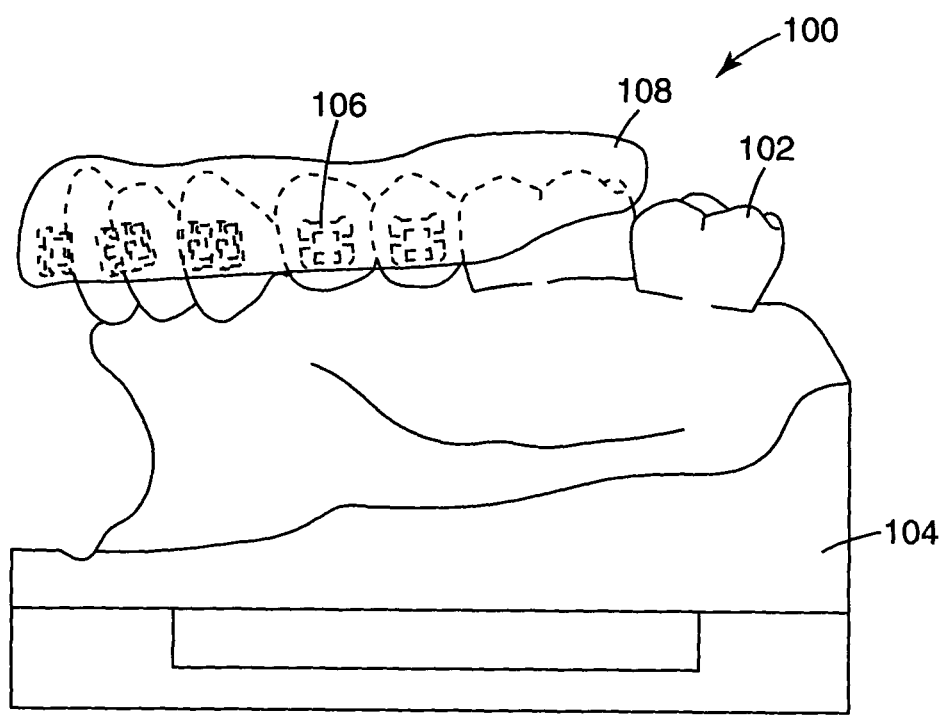
FIG. 8 is a side elevation view of an exemplary casting assembly.

FIG. 8 is a side elevation view of an exemplary casting assembly 100. The casting assembly 100 includes casting 102 on pedestal 104 with attached brackets 106, and an indirect bonding tray 108 formed over casting 102.

In another embodiment, a pedestal having embedded fiducial markers may be used to assist registration. For example, the pedestal may be constructed from plastic and have three or more beads embedded at known locations within the pedestal. The beads may be constructed of steel, lead, or any other material that may be detected by a scanning device and distinguished from the surrounding pedestal. The computer detects the scanned beads, and registers the physical model of the casting to the virtual model of the casting based on the known location of the fiducial markers within the pedestal. The process (described in FIGS. 2, 3A and 3B) and the advantages described herein apply to this alternative technique.

Figure 9:
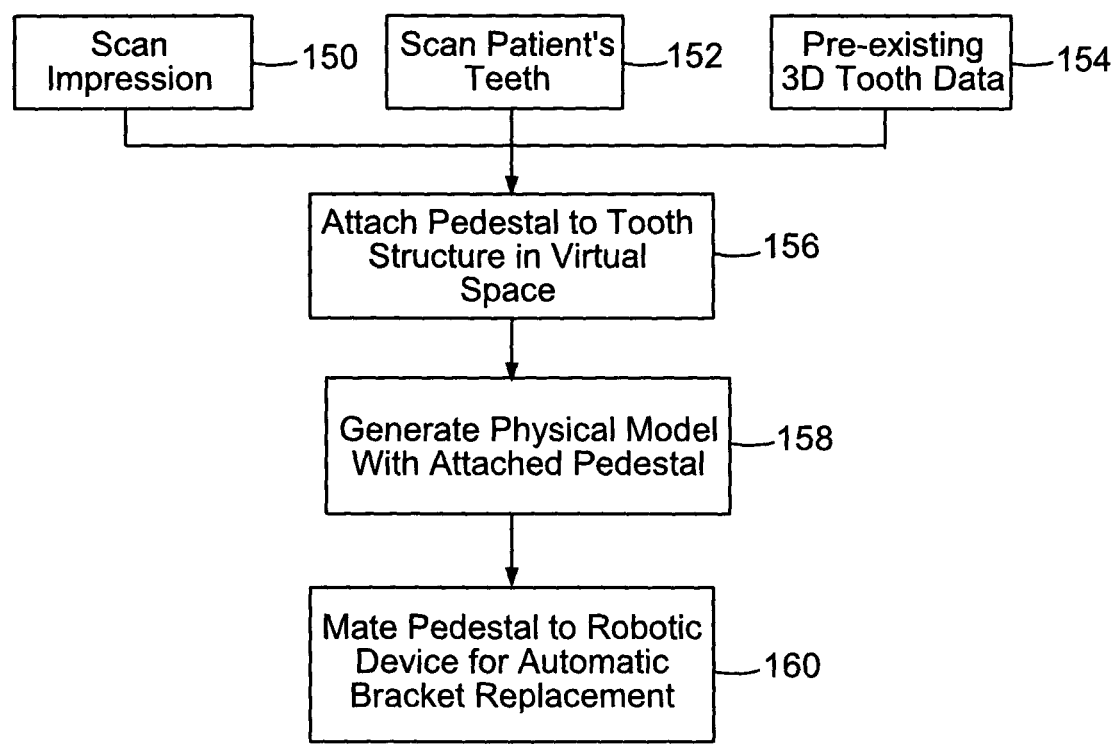
FIG. 9 is a block diagram of an exemplary process according to one embodiment of the invention.

FIG. 9 is a block diagram illustrating an exemplary process according to another embodiment of the invention in which a virtual pedestal of known geometry is attached to a digital tooth structure in a virtual environment. This process begins with a digital tooth structure generated by one of three techniques: scanning an impression of a patient's tooth structure (150), scanning the patient's teeth with an intra-oral scanner (152), or utilizing existing 3D tooth data (154). A user attaches a pre-existing CAD file of the pedestal to the digital tooth structure via software in the virtual environment (156). A rapid prototyping technique, such as stereolithography, utilizes the virtual tooth structure with attached pedestal to generate a physical model with attached pedestal (158). A user mates the physical pedestal to a robotic device for automatic bracket placement onto the physical model (160). As previously described, an orthodontic appliance, such as an indirect bonding tray, may be fabricated from the physical model with attached brackets.

In another embodiment, multiple components used during the process may be scanned in a specific sequence. For example, castings of the upper and lower arches, each with attached pedestals, may be sequentially scanned along with the patient's bite impression in the following sequence. First, an operator calibrates the scanner coordinate system to coincide with that of the CAD model of the pedestals, where the upper and lower pedestals are identical. An operator then scans the lower arch with pedestal, mates the bite impression to the lower arch, mates the upper arch to the bite impression, and then scans the upper arch with pedestal. Next, the operator uses software, such as Raindrop Geomagic Studio Best-Fit Alignment feature, to select only the upper arch pedestal from the upper arch scan data. The operator then uses the same software to align the virtual upper arch pedestal to the CAD model of the pedestal and records the transform. Next, the operator removes the lower arch from the scanner, scans just the upper arch with pedestal, and transforms the upper arch data points according the transform executed after the upper arch pedestal alignment step described above. This embodiment may be useful when utilizing optical scanners, which can only scan unobscured, visible surfaces. In addition to the advantages described herein, further advantages may include a method for semi-automatically setting the orientation between the upper and lower arches.

In another embodiment, multiple components used during the process may be simultaneous scanned. For example, castings of the upper and lower arches, each with attached pedestals, may be simultaneously scanned. In addition to the advantages described herein, further advantages may include a reduction in labor and cost by scanning all objects necessary for virtual bracket placement in a single scan, and a method for automatically or semi-automatically setting the orientation between the upper and lower arches by simultaneously scanning the two castings that are set in maximum intercuspation.

Furthermore, the invention may also enable simultaneous scanning of multiple castings, each with attached pedestal, and a bite impression, for one or more patients. In addition to the advantages described herein, this technique may be used to automatically or semi-automatically set the orientation between the upper and lower arches with the bite register, possibly eliminating the step of placing the castings in maximum intercuspation prior to the scan.

In another embodiment, dimples or other physical characteristics may be incorporated at known locations within an impression tray prior to scanning the impression tray. In particular, the impression tray may be scanned to generate a digital model of the impressions from a patient. The dimples or other physical characteristics of the impression tray may be used to aid the registration of the physical impression to the scanned impression. As described below in great detail, manufacturing facility 12 may further translate these physical characteristics to the casting during the formation of the casting; thus, allowing the registration to be maintained when placing the casting into a robotic device for automatic bracket placement per the digital model generated from the impression containing the dimples.

Figure 10A:
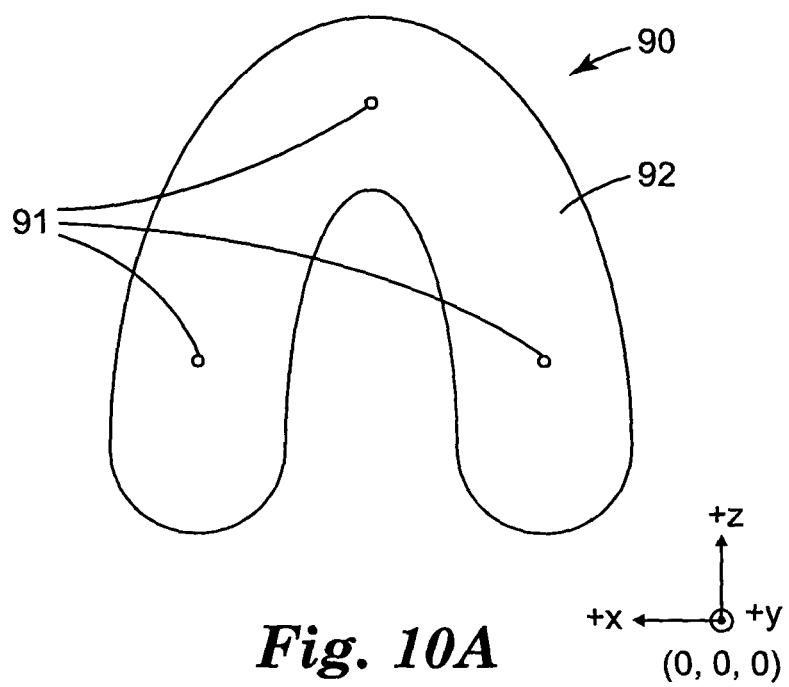
FIGS. 10A and 10B are an occlusal and distal view respectively of an exemplary impression tray with three hemispherical dimples.
Figure 10B:
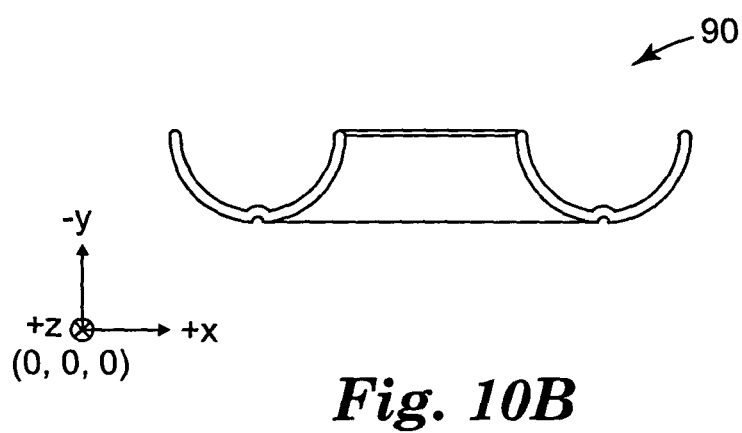

FIGS. 10A and 10B illustrate views of an exemplary impression tray 90 with three hemispherical dimples 91 in the occlusal surface 92 of the tray, from an occlusal and distal view respectively. The impression tray 90 is then mounted in a tripod configuration onto a main pedestal (not shown in FIGS. 10A and 10B), which has pillars or posts that correspond in shape and location to dimples 91 of impression tray 90. Dimples 91 may be of various shapes in various locations as long as they correspond with the pillars of the main pedestal.

Figure 11A:
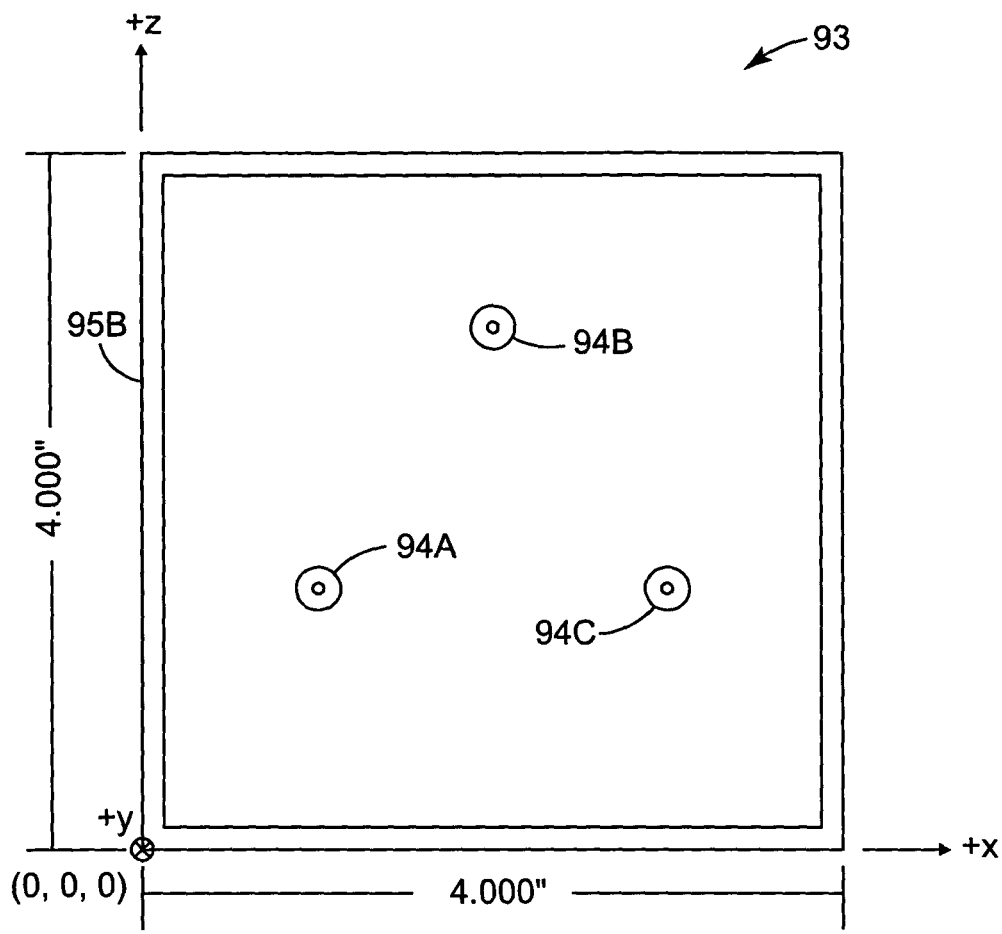
FIGS. 11A and 11B are a top and rear elevation view respectively of an exemplary main pedestal with three pillars.
Figure 11B:
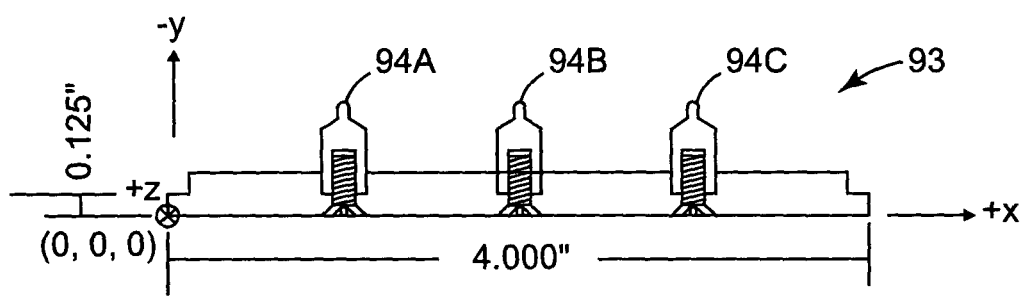

FIGS. 11A and 11B illustrate views of an exemplary main pedestal 93 with three pillars (posts) 94A, 94B and 94C, from a top and rear elevation view respectively. Main pedestal 93 (and three pillars 94A, 94B, 94C, upon which the impression tray sits), offer a corner and edges to which the points of the three pillars, and consequently all points in the dental impression, are registered in Cartesian space.

Next, in this example, since main pedestal 93 is a rectangular prism (except for material that is cut-out from the upper perimeter for the enclosing wall), the main pedestal mates into a right-angled corner of a scanner bed. Providing that such a right-angled corner is defined as the (0, 0, 0) origin of the scanner, and both the positive x- and positive z-axes extend parallel to and in the same direction as each of edges 95A, 95B of main pedestal 93, the main pedestal assumes the coordinate system of the scanner. Since main pedestal 93 is at a known location and orientation within the scanner, the impression tray, mounted to the main pedestal, is also oriented to the coordinate system of the scanner. Furthermore, utilization of additional right-angled corners of the scanner bed enables simultaneous scanning of multiple impressions.

Figure 12A:
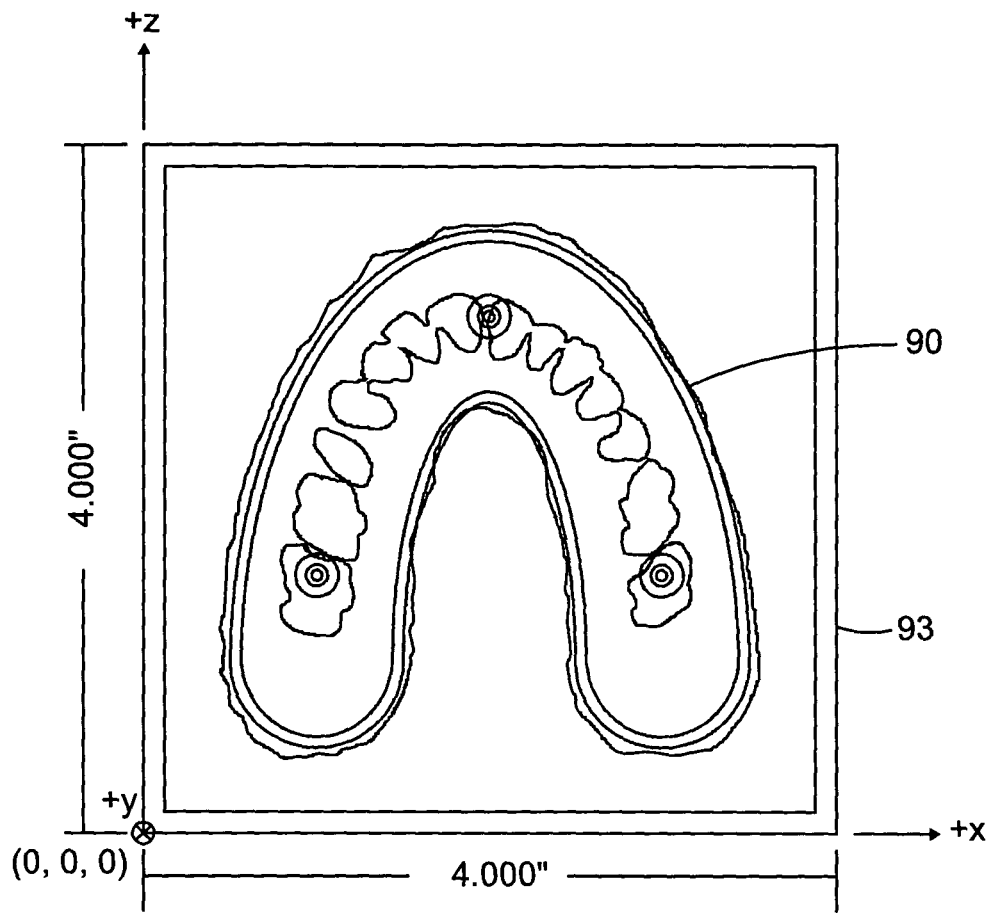
FIGS. 12A and 12B are a top and rear elevation view respectively of an exemplary impression tray attached to an exemplary main pedestal.
Figure 12B:
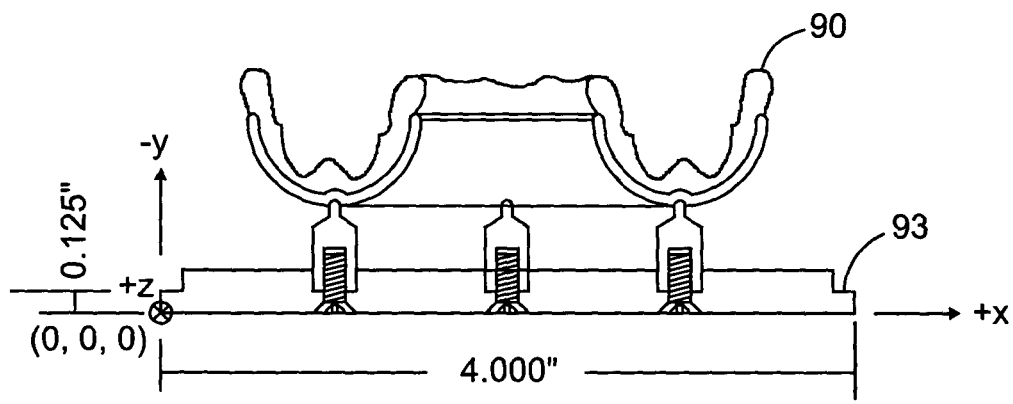

FIGS. 12A and 12B illustrate views of an exemplary impression tray attached to an exemplary main pedestal, from a top and rear elevation view respectively. In particular, FIG. 12A is a top view and FIG. 12B is a side view of impression tray 90 attached to main pedestal 93.

In order to form a casting model that remains in registration with the dental impression and the digital model, the casting formation process may utilize an inverted pedestal that sits atop an enclosing wall that rests on the main pedestal. In this example, the enclosing wall is shaped like a rectangular tube that is open at opposite ends (top and bottom) and fits into the cut-out perimeter of the top of the main pedestal. The height of the enclosing wall is constant about its circumference.

Figure 13:
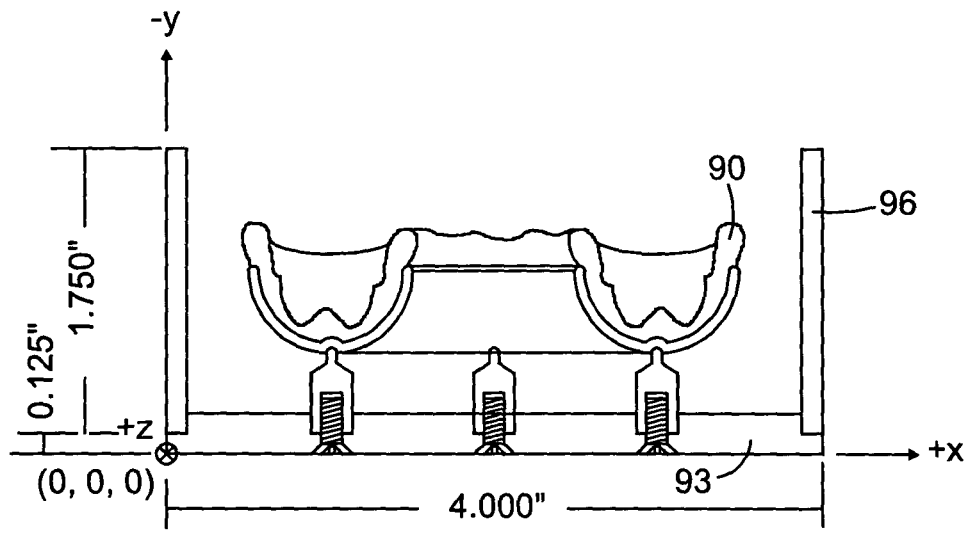
FIG. 13 is a rear elevation view of an exemplary enclosing wall resting on a main pedestal with attached impressions.

FIG. 13 illustrates a rear elevation view of an exemplary enclosing wall 96 resting on main pedestal 93 with attached impression 90. The enclosing wall 96 may be fitted into a cut-out perimeter of a top of main pedestal 93 either before or after pouring liquid casting material into the impression.

One purpose of the enclosing wall is to provide a constant vertical translation from the bottom of the main pedestal to the top of an inverted pedestal that rests atop the enclosing wall. The top of the inverted pedestal later becomes the bottom of the same pedestal as the inverted pedestal is inverted and placed on the bed of the multi-axis robot. Both the inverted pedestal and the main pedestal have cut-out perimeters to fit the enclosing wall and allow the enclosing wall to rest completely in the depths of the cutouts. Because the thicknesses (or heights) of the pedestals, the depths of their cut-out perimeters, and the height of the enclosing wall are all of known, constant dimensions, the distance between the bottom of the main pedestal and the top of the inverted pedestal is also a constant, known distance. This distance becomes an important translation when transforming coordinates between different machine coordinate systems. Another purpose of the enclosing wall, especially with regard to its joinery with the pedestals, is to keep the inverted pedestal in precise alignment with the main pedestal. The enclosing wall keeps a constant distance between the bottom planes of both pedestals and also keeps the pedestals from otherwise rotating or translating with respect to one another.

To maintain registration after pouring the casting material, the inverted pedestal forms a connection with the casting. Thus, prior to use, the inverted pedestal is drilled and tapped with a number of threaded holes for receiving machine screws.

Figure 14:
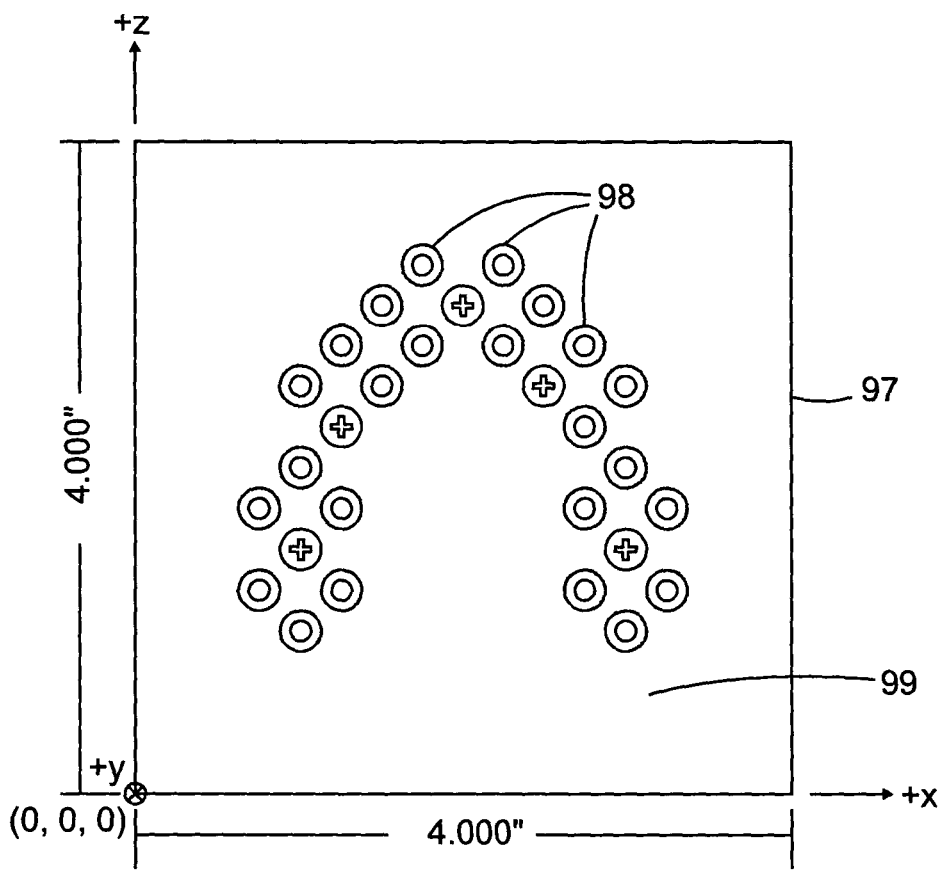
FIG. 14 is a top view of an exemplary inverted pedestal drilled with holes and tapped with machine threads.

FIG. 14 is a top view of an exemplary inverted pedestal 97 drilled with holes 98 (only a subset are labeled in FIG. 13 for simplicity and clarity). Holes 98 are tapped with machine threads for receiving screws. After pouring the casting material into the impression, inverted pedestal 97 is fitted to the top of enclosing wall 96, and three or more screws are threaded into holes 98. Hole location and depth may be based on the following criteria: the screws are adequately spaced apart from one another, each screw descends into the liquid casting material without coming into contact with the area where the casting material contacts the impression material, and each screw descends into the casting material sufficiently far to be held strongly when the casting material solidifies. An inverted pedestal fabricated from a clear solid material, such as Lexan® (polycarbonate plastic) or Plexiglass (acrylic plastic), may facilitate viewing through the inverted pedestal, making it easier to meet the above criteria. If using a photopolymer casting material, a clear inverted pedestal also allows transmission of an external light source for curing the casting material.

Since a top-most surface 99 of inverted pedestal 97 (FIG. 14) might otherwise later come into contact with a manufacturing fixture for automatic bracket placement, the top-most surface of the inverted pedestal is sufficiently displaced from the drilled and tapped surface of the inverted pedestal to prevent screw-heads from intersecting the plane intended for contact with the robotic device or CNC equipment. A surrounding wall extending vertically with a constant height from the inverted pedestal achieves this displacement. In order to ensure proper registration, the surrounding wall of the inverted pedestal extends to the same perimeter as the enclosing wall and main pedestal.

Figure 15:
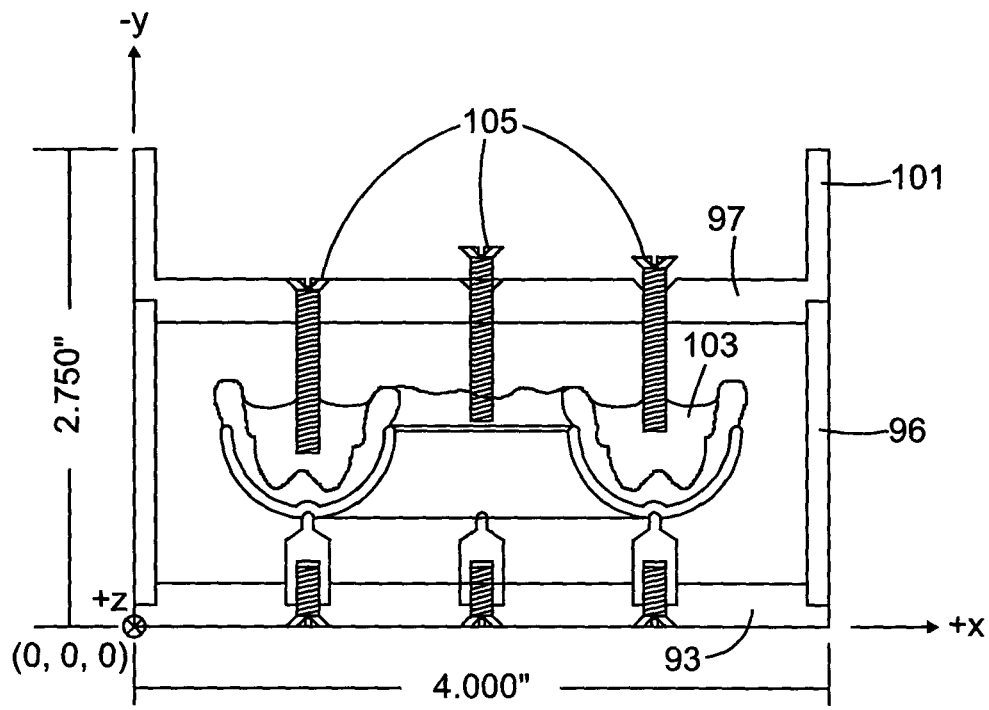
FIG. 15 is a rear elevation view of an exemplary inverted pedestal fitted and properly aligned with screws strategically located and threaded into the casting material, upon a main pedestal, with an enclosing wall.

FIG. 15 is a rear elevation view of an exemplary inverted pedestal 97 with surrounding wall 101 fitted and properly aligned with screws 105 strategically located and threaded into casting material 103, upon main pedestal 93, with enclosing wall 96. As liquid casting material 103 cures into a solid, screws 105 secure the position of casting 103 with respect to inverted pedestal 97.

Consequently, the distance between the casting and the inverted pedestal becomes fixed, regardless of whether the screws are turned or not (because both the holes in the inverted pedestal and the holes formed in the casting have the same thread). Further, due to the multiplicity of screws, the torque resulting from the turning of a single screw does not cause the casting to rotate with respect to the inverted pedestal. These features make it possible to remove the casting from the inverted pedestal and later restore the casting's position without error, if desired, provided that the same assembly of parts is used to help the screws enter the casting with the same number of threads between the casting and the inverted pedestal.

After the liquid casting material cures into a solid, an operator at manufacturing facility 12 removes the inverted pedestal from the enclosing wall and main pedestal. The impression (and impression tray) will likely remain attached to the casting until the operator applies force to separate the casting from the impression tray. The operator then inverts the inverted pedestal and places the inverted pedestal on a fixture of manufacturing equipment such that the surrounding wall of the inverted pedestal is in contact with the manufacturing fixture and the occlusal surfaces of the teeth in the casting are facing up. Since, in this example, the inverted pedestal is a rectangular prism, similar to the main pedestal (except for material that is cut-out from the [now] upper perimeter), the inverted pedestal is mated into a right-angled corner on the fixture of manufacturing equipment, such as a multi-axis robotic device. Providing that such a right-angled corner is defined as (0, −2.75, 0) [in this example only] in the coordinate system of the robot, and each positive axis extends parallel to and in the same direction as each edge of the rectangular prismatic inverted pedestal, the inverted pedestal assumes the coordinate system of the robot with a single translation.

Figure 16:
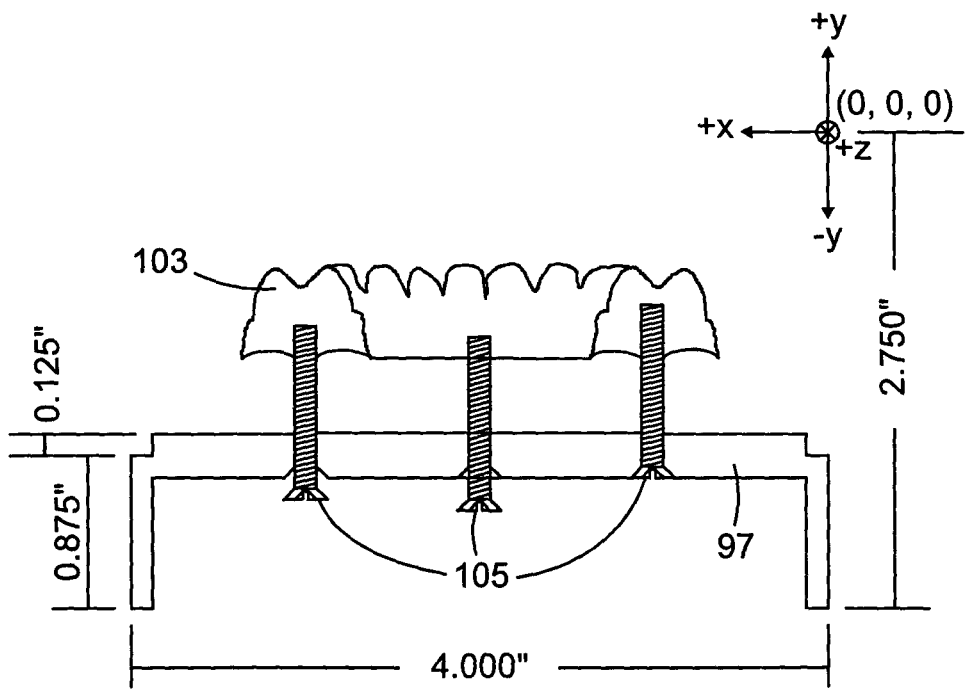
FIG. 16 is an inverted rear elevation view of an exemplary inverted pedestal with screws securing the position of the solid casting.

FIG. 16 is an inverted rear elevation view of an exemplary inverted pedestal 97 with screws 105 securing the position of the solid casting 103.

An alternative embodiment of the invention uses registration markers arbitrarily placed directly on three or more of the patient's teeth prior to forming the impression. In this embodiment, manufacturing facility 12 need not attach pedestals to the castings, since clinic 8 attaches the registration markers directly to the patient's teeth. After the markers are in place, techniques of this embodiment involve scanning the impression or utilizing an intra-oral scanner to scan the patient's tooth structure to generate a digital model of the tooth structure. The registration markers on the patient's teeth are used to register the digital model with the physical impression. Alternatively, a casting may be created from the impression formed from the patient's teeth having markers. During the casting formation, the markers transfer to the casting such that a scan of the casting generates a digital model of the tooth structure, and the registration markers on the patient's teeth are used to register the digital model with the physical casting.

Figure 17:
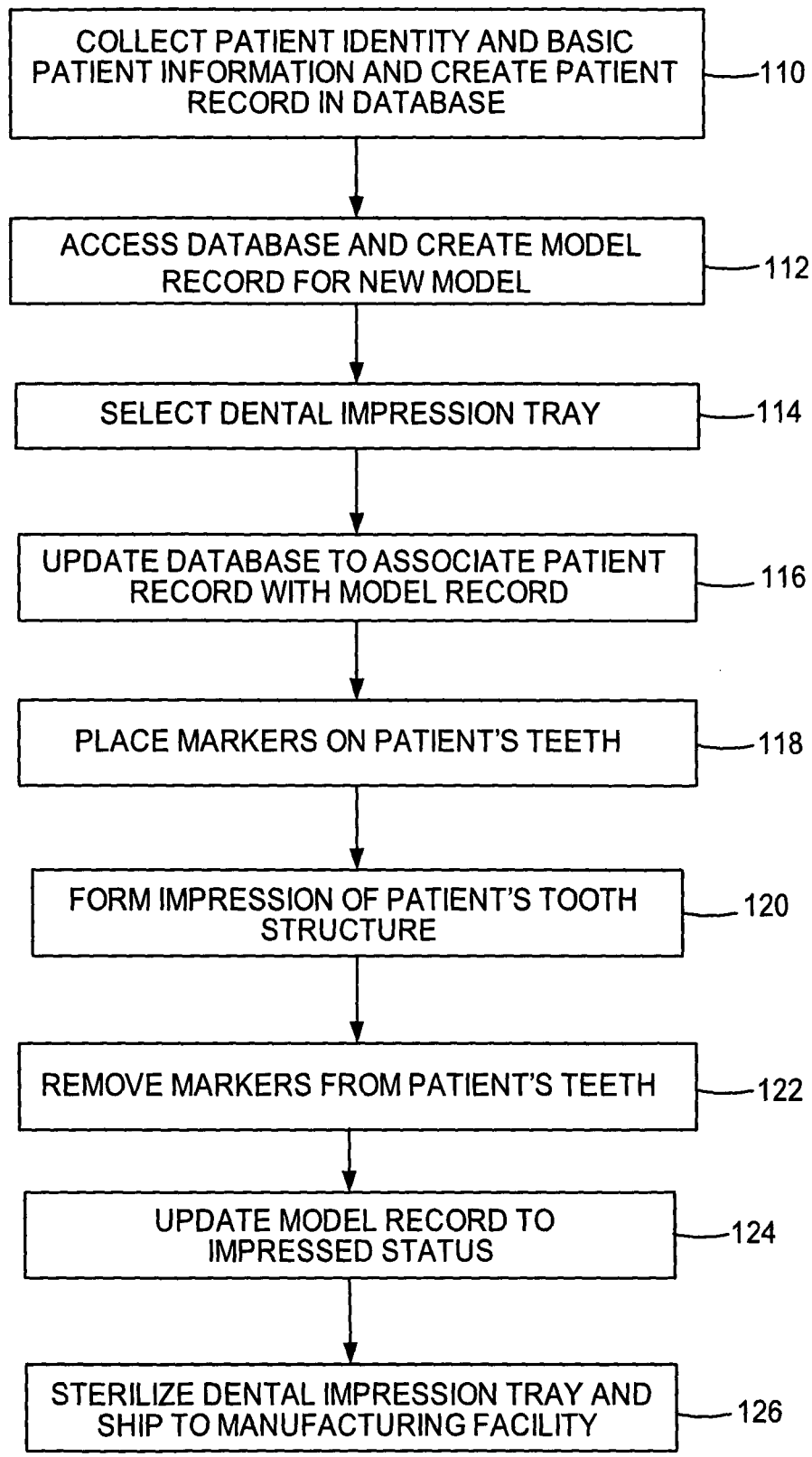
FIG. 17 is block diagram illustrating an exemplary process at a clinic, distinguishable from FIGS. 3A and 3B by the placement of marker brackets at the clinic.

FIG. 17 is a block diagram illustrating an exemplary process at clinic 8 for placing registration markers directly on a one or more of the patient's teeth prior to forming the impression. Practitioner at clinic 8 collects patient identity and creates patient record in database (110). Next, the practitioner at clinic 8 creates a new model record (112) and selects a dental impression tray (114). The practitioner then updates the database to associate patient record with model record (116).

Prior to forming the impression, an orthodontist of clinic 8 places markers on the patient's teeth (118). In this embodiment, three registration markers may be attached to each of the upper and lower arches. At least three types of markers may be utilized for this registration technique; a metallic hemispherical bracket, a cured hemisphere of adhesive, or a light transmitting marker bracket, and the markers may be placed on a single tooth or distributed across different teeth. The cured hemisphere of adhesive contains a polymeric substance such as an orthodontic adhesive, a dental restorative, or a cyanoacrylate.

Next, the orthodontist of clinic 8 forms an impression of the patient's tooth structure after all tooth markers are in place (120). The orthodontist of clinic 8 then removes the markers from the patient's teeth (122). In one embodiment, marker attachment does not require any etching or priming of the teeth. As a result, removal of the markers may involve minimal trauma to the patient. The practitioner of clinic 8 then updates the model record to an "impressed" status (124), and sterilizes and ships impression tray 10 to manufacturing facility 12 (126). Manufacturing facility 12 scans in the impression with markers to generate a digital model of the patient's tooth structure. As an alternative to scanning the impression of the teeth with the markers, the orthodontist of clinic 8 may utilize an intra-oral scanner to scan the teeth with markers.

An alternative embodiment of the invention involves forming the patient's impression, without placing markers on the patient's teeth, and then arbitrarily placing registration markers onto the formed impression. Yet another alternative embodiment involves forming the patient's impression, without placing markers on the patient's teeth, forming a casting from the impression, and then arbitrarily placing registration markers onto the formed casting. After placing the registration markers onto the impression or casting, manufacturing facility 12 scans the impression or casting with registration markers to generate a digital model of the impression or casting with attached registration markers.

Typically, the scanned model generates a point cloud data file. Manufacturing facility 12 surfaces the point cloud data file, and may use one of several commercial software packages. For example manufacturing facility 12 may utilize a software package under the trade designation of "Wrap" or "Studio" available from Raindrop Geomagic, Inc. of Durham, N.C. Once the point cloud is surfaced, a 3D digital model of the tooth structure exists in the computer. Manufacturing facility 12 utilizes a software algorithm to identify the registration markers for registering a coordinate system of the physical model of the tooth structure to a coordinate system of the 3D digital model.

Figure 18:
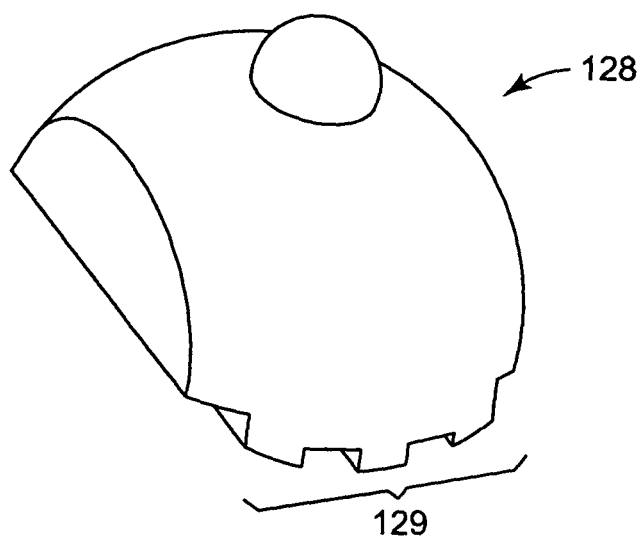
FIG. 18 is a perspective view of an exemplary metallic hemispherical bracket.

FIG. 18 is a perspective view of an exemplary metallic hemispherical bracket 128, which has a machined base 129 that may be affixed to the patient's teeth prior to scanning. A bracket manufacturer may add a bonding pad pre-coated with orthodontic adhesive to machined base 129. The orthodontist of clinic 8 manually attaches metallic hemispherical bracket 128 with adhesive to the patient's tooth. Alternatively, the orthodontist may attach a light curable adhesive to bracket 128 and utilize a light transmitting marker tool to attach marker bracket 128 to the patient's tooth.

Another type of marker is a light transmitting marker bracket that an orthodontist may attach to the surface of the tooth by using a light transmitting marker tool and a light curable adhesive such as Transbond adhesive. The light transmitting marker bracket may be a ceramic or metal bracket with a transparent channel cut through the bracket. Alternatively, the orthodontist may cure a hemisphere of light curable adhesive to the tooth with the light transmitting marker tool, such that the hemisphere of adhesive serves as the registration marker.

Figure 19:
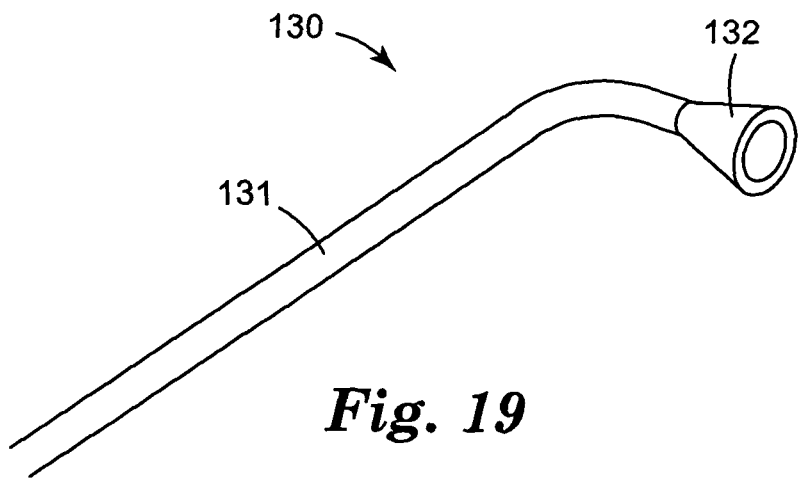
FIG. 19 is a perspective view of an exemplary marker tool for attaching marker brackets to a patient's tooth.

FIG. 19 is a perspective view of an exemplary light transmitting marker tool 130 for attaching a light transmitting marker to a tooth of a patient prior to scanning. The marker tool consists of a handle 131 and a clear bell housing 132. The handle may be constructed of any stiff material, but is preferably constructed of a light transmitting material such as a fiber optic light guide. The clear bell housing allows a large percentage of light to transmit through the housing. The bell housing has a hemispherical cup cut into the housing.

Figure 20:
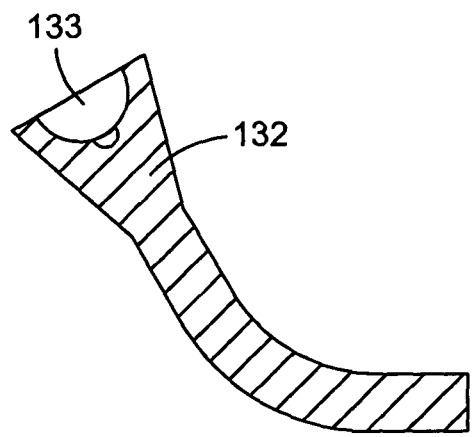
FIG. 20 is a cross section of an exemplary hemispherical cup in bell housing of a marker tool.

FIG. 20 is a cross section of the hemispherical cup 133 coupled to bell housing 132 of light transmitting marker tool 130 for placement on a tooth. The orthodontist of clinic 8 fills cup 133 with a light curable adhesive (such as a dental or orthodontic adhesive or a dental restorative) and uses handle 131 to place the adhesive against the surface of the tooth. In some embodiments, the adhesive alone may be the registration marker. For example, the adhesive may include metalized particles capable of being detected within the scan data. Alternatively, the orthodontist of clinic 8 may attach a light transmitting marker bracket to the cup and use the handle to place the bracket against the surface of the tooth to cure the adhesive with attached bracket into place on the tooth. After the adhesive cures, the orthodontist of clinic 8 removes the marker tool from the patient's mouth.

Figure 21:
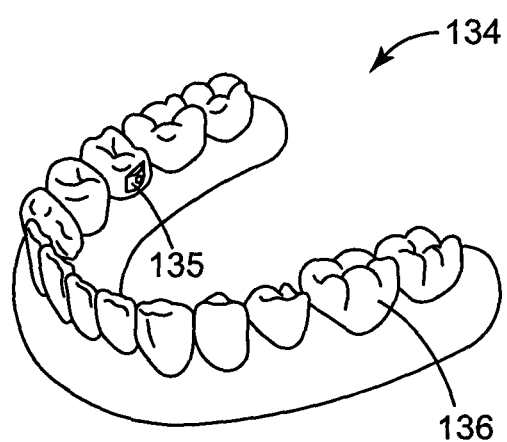
FIG. 21 is a perspective view of an exemplary surfaced 3D digital model with a marker bracket.

FIG. 21 is a perspective view of a surfaced 3D digital model 134 with a hemispherical marker bracket 135 on a virtual tooth structure 136. Manufacturing facility 12 utilizes a software algorithm to identify the marker brackets for registering a coordinate system of the physical model of the tooth structure to a coordinate system of the 3D digital model. In one embodiment, a high-pass filter masks out the lower density impression or casting material in order to identify the hemispherical markers that are of a higher density. Next, an algorithm computes the centroid of each sphere. In another embodiment, an operator visually identifies each hemispherical marker bracket in the scan and uses a virtual probe to sample four or more points from each hemisphere. Next, a simple sphere equation determines each hemisphere center.

Clinic 8 then uses the registered digital model for virtual bracket placement and/or to assist automatic or semi-automatic manufacturing process. Prior to automatically placing the physical brackets onto the casting which contains the markers, manufacturing facility 12 registers the casting with the robotic system. In one embodiment, a physical probe attached to the robot samples four or more points from the surface of each hemispherical marker and computes the hemisphere centers in a manner similar to that of the virtual probe described above. The physical probe may be a touch-trigger probe or a laser-range finder. Next, transform software, such as the Best-Fit Alignment feature in Raindrop Geomagic Studio, transforms the data points in the scanned model from scanner coordinates to robotic coordinates. Now, manufacturing facility 12 may utilize the registered digital model for automatic orthodontic bracket placement onto the casting by replacing the robotic physical probe with an end-effector for placing orthodontic brackets onto the casting in the same relative positions and orientations specified in the virtual world. Alternatively, the registration process of this embodiment may be implemented with hemispheres attached to a pedestal that is physically bonded to the casting.

Alternatively, manufacturing facility 12 may utilize a CNC machined plate as a fixture for the casting during robotic placement of the brackets onto the casting. In order to do so, manufacturing facility 12 may fabricate a CNC machined plate that has the surface profile of the patient's teeth machined into the plate. The digital model is used as a geometric pattern to control the CNC device to form the surface profile in the plate.

Figure 22:
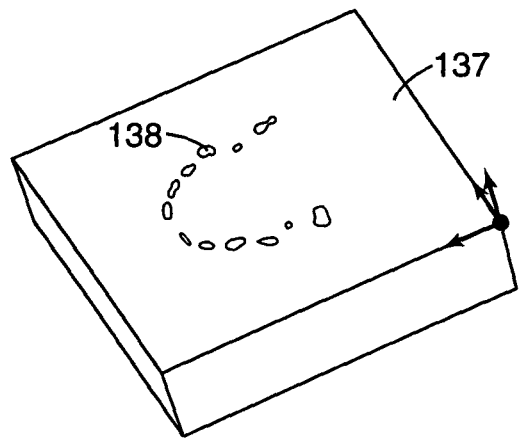
FIG. 22 is a perspective view of an exemplary CNC machined plate with a surface profile machined into it.

FIG. 22 is a perspective view of an exemplary CNC machined plate 137 with surface profile 138 machined into plate 137. After machining surface profile 138, the casting may be set into surface 138 on plate 137.

Figure 23:
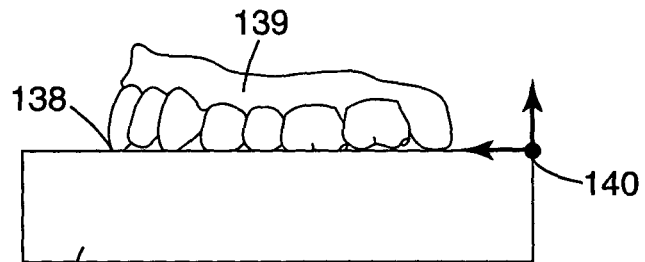
FIG. 23 is a side view of a casting set into the machined surface of an exemplary plate.

FIG. 23 is a side view of a casting 139 set into the machined surface 138 of plate 137. The corner of the plate, 140, represents a coordinate system of the plate, which has a known location with respect to the patient's surface profile machined into the plate. Thus, when manufacturing facility 12 places the casting into the surface of the plate, all six degrees of freedom for the casting are known with respect to the corner coordinate system. Furthermore, the digital model is registered to the corner coordinate system because the location of the CNC surface data is known with respect to the corner coordinate system.

Figure 24:
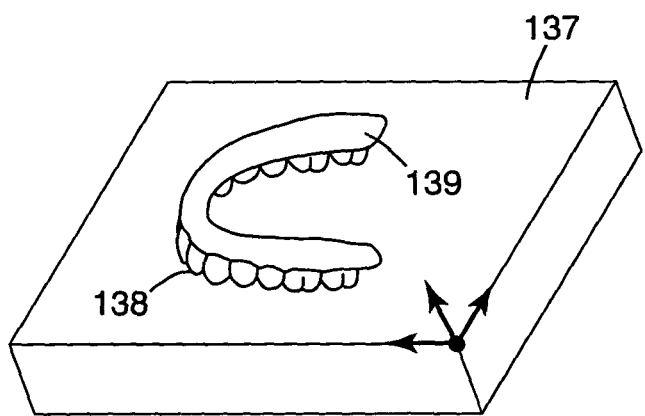
FIG. 24 is a perspective view of a casting set into the machined surface of an exemplary plate.

FIG. 24 is a perspective view of casting 139 set into machined surface 138 of plate 137. After robotic equipment places the brackets onto casting 139, manufacturing facility 12 forms indirect bonding tray 16 on casting 139 and forwards the tray to clinic 8 for use on patient 6.

Various implementations and embodiments of the invention have been described. Nevertheless, it is understood that various modifications can be made without departing form the invention. These and other embodiments are within the scope of the following claims.

The invention claimed is:

1. A method for registering a coordinate system of a physical model of a patient's tooth structure to a coordinate system of a digital model of the tooth structure, the method comprising:
    forming the physical model of the patient's tooth structure;
    attaching a pedestal having a known physical characteristic to the physical model;
    scanning the physical model and the pedestal to generate the digital model of the tooth structure and the pedestal;
    with a computer, registering the physical model to the digital model based on the known physical characteristic of the pedestal; and
    mating the pedestal of known physical characteristic into a fixture of manufacturing equipment and registering coordinate systems of the physical and digital models to a coordinate system of the manufacturing equipment.

2. The method of claim 1, wherein forming the physical model of the patient's tooth structure comprises forming a casting of the patient's tooth structure.

3. The method of claim 1, wherein forming the physical model of the patient's tooth structure comprises forming an impression of the patient's tooth structure.

4. The method of claim 1, wherein attaching the pedestal of known physical characteristic to the physical model comprises attaching a pedestal of known geometry to the physical model.

5. The method of claim 1, wherein attaching the pedestal of known physical characteristic to the physical model comprises attaching a pedestal having fiducial markers at known locations on the pedestal.

6. The method of claim 5, wherein attaching a pedestal having fiducial markers at known locations on the pedestal comprises embedding metal beads within the pedestal at known locations.

7. The method of claim 1, wherein scanning the physical model and the pedestal to generate the digital model of the tooth structure and the pedestal comprises placing the physical model and the pedestal in a scanner without limitation to a specified orientation.

8. The method of claim 1, wherein scanning the physical model and the pedestal to generate the digital model of the tooth structure and the pedestal comprises placing the physical model with pedestal in a scanner fixture at a known location.

9. The method of claim 8, wherein registering the physical model to the digital model comprises registering the physical model to the digital model using both the known physical characteristic of the pedestal and the known location of the scanner fixture.

10. The method of claim 1, wherein registering the physical model to the digital model comprises determining a best-fit between pedestal data from the scanned physical model and data from a pre-existing CAD file of the pedestal.

11. The method of claim 1, wherein mating the pedestal of known physical characteristic into the fixture of manufacturing equipment comprises mating the pedestal of known physical characteristic with a robotic device fixture configured for automatic bracket placement onto the physical model attached to the pedestal.

12. The method of claim 11, further comprising: attaching, with the robotic device fixture, brackets to the physical model; and forming an indirect bonding device upon the physical model having the attached brackets.

13. The method of claim 1, wherein mating the pedestal of known physical characteristic into the fixture of manufacturing equipment comprises mating the pedestal of known physical characteristic with a trimming fixture for trimming an indirect bonding device.

14. The method of claim 13, further comprising, with the manufacturing equipment, trimming the indirect bonding device while the indirect bonding device is on the physical model attached to the pedestal of known physical characteristic.

15. The method of claim 13, further comprising, with the manufacturing equipment, trimming the indirect bonding device, wherein trimming the indirect bonding device comprises transferring a coordinate system of the physical model to a coordinate system of the indirect bonding device for trimming the indirect bonding device after removing indirect bonding device from the physical model.

16. The method of claim 1, further comprising attaching a second pedestal to the physical model, the second pedestal being configured for registering coordinate systems of the physical and digital models to a coordinate system of the manufacturing equipment.

17. A system comprising:
    a physical model of a patient's tooth structure;
    a pedestal having a known physical characteristic configured for registration of the pedestal and the physical model within a 3D environment using a computer, wherein the pedestal is attached to the physical model; the computer that is configured to register the physical model to a digital model of the physical model based on the known physical characteristic of the pedestal, and a manufacturing equipment comprising a fixture configured to mate with the pedestal of known physical characteristic to register coordinate systems of the physical and digital models to a coordinate system of the manufacturing equipment.

18. The system of claim 17, wherein the physical model of a patient's tooth structure is formed by casting.

19. The system of claim 17, wherein the physical model of a patient's tooth structure is formed by taking an impression.

20. The system of claim 17, wherein the pedestal of known physical characteristic comprises a pedestal of known geometry.

21. The system of claim 17, wherein the pedestal of known physical characteristic comprises a pedestal containing fiducial markers at known locations.

22. The system of claim 21, wherein the fiducial markers comprise metal beads embedded at known locations.

23. The system of claim 17, wherein the computer is configured to register the coordinate systems of the physical and digital models to the coordinate system of the manufacturing equipment.

24. A system comprising:
a physical model of a tooth structure attached to a pedestal having a known physical characteristic;
a scanner that scans the physical model with attached pedestal to generate a digital model of the tooth structure and the pedestal;
a computer that registers the physical model to the digital model with the known physical characteristic of the pedestal; and
a manufacturing equipment comprising a fixture configured to mate with the pedestal of known physical characteristic to register coordinate systems of the physical and digital models to a coordinate system of the manufacturing equipment.

25. The system of claim 24, wherein the physical model of a tooth structure is formed by casting.

26. The system of claim 24, wherein the physical model of a tooth structure comprises an impression.

27. The system of claim 24, wherein the pedestal of known physical characteristic comprises a pedestal of known geometry.

28. The system of claim 24, wherein the pedestal of known physical characteristic comprises a pedestal having fiducial markers at known locations that are constructed of metal beads.

29. The system of claim 24, wherein the scanner comprises a fixture at a known location for receiving the physical model.

30. The system of claim 29, wherein the computer utilizes the known characteristic of the pedestal and the known location of the scanner fixture to register the physical model to the digital model.

31. The system of claim 24, wherein the computer registers the physical model to the digital model with an algorithm that determines a best-fit between pedestal data from the scanned physical model and data from a pre-existing CAD file of the pedestal.

32. The system of claim 24, further comprising a second pedestal attached to the physical model, the second pedestal being configured for registering coordinate systems of the physical and digital models to a coordinate system of the manufacturing equipment.

33. A method for registering a coordinate system of a physical model of a patient's tooth structure to a coordinate system of a digital model of the tooth structure, the method comprising:
generating the digital model of a tooth structure;
with a computer, attaching a virtual pedestal of known physical characteristic to the digital model;
generating the physical model of the tooth structure with an attached physical pedestal of known physical characteristic from the digital model with the attached virtual pedestal of known physical characteristic, wherein the physical pedestal is configured to mate with a fixture of manufacturing equipment; and
mating the pedestal of known physical characteristic into a fixture of manufacturing equipment and registering coordinate systems of the physical and digital models to a coordinate system of the manufacturing equipment.

34. The method of claim 33, wherein generating the digital model comprises scanning the tooth structure.

35. The method of claim 34, wherein scanning the tooth structure comprises utilizing an intra-oral scanner.

36. The method of claim 33, wherein generating the digital model comprises scanning an impression of the tooth structure.

37. The method of claim 33, wherein generating the physical model of the tooth structure comprises utilizing rapid prototyping method.

38. The method of claim 33, wherein mating the physical pedestal of known physical characteristic into the fixture of manufacturing equipment comprises mating the physical pedestal of known physical characteristic into a robotic device fixture configured for automatic bracket placement onto the physical model attached to the pedestal.

* * * * *

UNITED STATES PATENT AND TRADEMARK OFFICE
CERTIFICATE OF CORRECTION

| | |
|---|---|
| PATENT NO. | : 8,491,306 B2 |
| APPLICATION NO. | : 11/195954 |
| DATED | : July 23, 2013 |
| INVENTOR(S) | : Richard E. Raby et al. |

It is certified that error appears in the above-identified patent and that said Letters Patent is hereby corrected as shown below:

In the Claims

Column 19, line 44, delete "comprises an impression." and insert
-- is formed by taking an impression. --

Signed and Sealed this
Thirty-first Day of December, 2013

Margaret A. Focarino
*Commissioner for Patents of the United States Patent and Trademark Office*